United States Patent
Lemmer et al.

(10) Patent No.: US 12,429,435 B2
(45) Date of Patent: Sep. 30, 2025

(54) SYSTEMS AND METHODS TO CONFIGURE RADIOGRAPHY SYSTEMS

(71) Applicant: Illinois Tool Works Inc., Glenview, IL (US)

(72) Inventors: Camaron Lemmer, Saint Michael, MN (US); Brett Muehlhauser, Prior Lake, MN (US)

(73) Assignee: Illinois Tool Works Inc., Glenview, IL (US)

( * ) Notice: Subject to any disclaimer, the term of this patent is extended or adjusted under 35 U.S.C. 154(b) by 256 days.

(21) Appl. No.: 18/352,104

(22) Filed: Jul. 13, 2023

(65) Prior Publication Data

US 2024/0019384 A1    Jan. 18, 2024

Related U.S. Application Data

(60) Provisional application No. 63/389,664, filed on Jul. 15, 2022.

(51) Int. Cl.
  *G01N 23/04*    (2018.01)
  *A61B 6/00*    (2024.01)
  (Continued)

(52) U.S. Cl.
  CPC .......... *G01N 23/04* (2013.01); *A61B 6/545* (2013.01); *A61B 6/56* (2013.01); *G06T 5/73* (2024.01);
  (Continued)

(58) Field of Classification Search
  CPC .......... G01N 23/04; G01N 2223/401; G01N 2223/302; G01N 2223/303;
  (Continued)

(56) References Cited

U.S. PATENT DOCUMENTS

| | | | |
|---|---|---|---|
| 4,763,343 A | 8/1988 | Yanaki | |
| 8,184,768 B2 * | 5/2012 | Honda | A61B 6/542 378/8 |
| 2010/0158318 A1 | 6/2010 | Snoeren | |

FOREIGN PATENT DOCUMENTS

| | | |
|---|---|---|
| DE | 102020112651 | 11/2021 |
| JP | 2004081331 | 3/2004 |
| JP | 2010158257 | 7/2010 |

OTHER PUBLICATIONS

Int'l Search Report and Written Opinion Appln No. PCT/US2023/070226 mailed Oct. 18, 2023.

* cited by examiner

*Primary Examiner* — Courtney D Thomas
(74) *Attorney, Agent, or Firm* — McAndrews, Held & Malloy, Ltd.

(57) ABSTRACT

An example method to configure a radiography system having a radiation emitter and a radiation detector involves: analyzing, using processing circuitry, a reference image captured using a first value of a first power parameter for the radiation emitter to determine a value of a focal spot size for the radiation emitter; based on a determined relationship between the first value of the first power parameter and the value of the focal spot size, output an indication of whether a selected value of the first power parameter results in a value of an unsharpness parameter satisfying a threshold unsharpness value; and control the radiography system using the selected power parameter to perform a radiography process to obtain one or more radiographic images that satisfy the threshold unsharpness value.

20 Claims, 10 Drawing Sheets

(51) Int. Cl.
  *G06T 5/73*    (2024.01)
  *G06T 7/00*    (2017.01)
  *G06T 7/60*    (2017.01)

(52) U.S. Cl.
  CPC .............. *G06T 7/0002* (2013.01); *G06T 7/60* (2013.01); *G01N 2223/401* (2013.01); *G06T 2200/24* (2013.01); *G06T 2207/10116* (2013.01); *G06T 2207/30168* (2013.01)

(58) Field of Classification Search
  CPC ........ G01N 2223/304; G01N 2223/321; A61B 6/545; A61B 6/56; A61B 6/582; A61B 6/54; G06T 5/73; G06T 7/0002; G06T 7/60; G06T 2200/24; G06T 2207/10116; G06T 2207/30168
  See application file for complete search history.

SYSTEMS AND METHODS TO CONFIGURE RADIOGRAPHY SYSTEMS

RELATED APPLICATIONS

The present application claims the benefit of U.S. Provisional Patent Application Ser. No. 63/389,664, filed Jul. 15, 2022, entitled "Systems and Methods to Configure Radiography Systems." The entirety of U.S. Provisional Patent Application Ser. No. 63/389,664 is expressly incorporated herein by reference.

TECHNICAL FIELD

The present disclosure generally relates to industrial radiography imaging processes and, more particularly, to systems and methods to configure radiography systems.

BACKGROUND

Industrial radiography imaging systems are used to acquire two dimensional (2D) radiographic images, 2D sinograms, and/or three-dimensional (3D) volumetric data of parts used in industrial applications. Such industrial applications might include, for example, aerospace, automotive, electronic, medical, pharmaceutical, military, and/or defense applications. The 2D radiographic images may be evaluated to check the part(s) for cracks, flaws, defects, discontinuities, and/or anomalies that may or may not normally be visible to the human eye, and/or to determine internal and/or external measurements of part(s).

Limitations and disadvantages of conventional and traditional approaches will become apparent to one of skill in the art, through comparison of such systems with the present disclosure as set forth in the remainder of the present application with reference to the drawings.

BRIEF SUMMARY

The present disclosure is directed to systems and methods to configure radiography systems, substantially as illustrated by and/or described in connection with at least one of the figures, and as set forth more completely in the claims.

These and other advantages, aspects and novel features of the present disclosure, as well as details of an illustrated example thereof, will be more fully understood from the following description and drawings.

BRIEF DESCRIPTION OF THE DRAWINGS

The figures are not necessarily to scale. Where appropriate, the same or similar reference numerals are used in the figures to refer to similar or identical elements.

DETAILED DESCRIPTION

Figure 1:
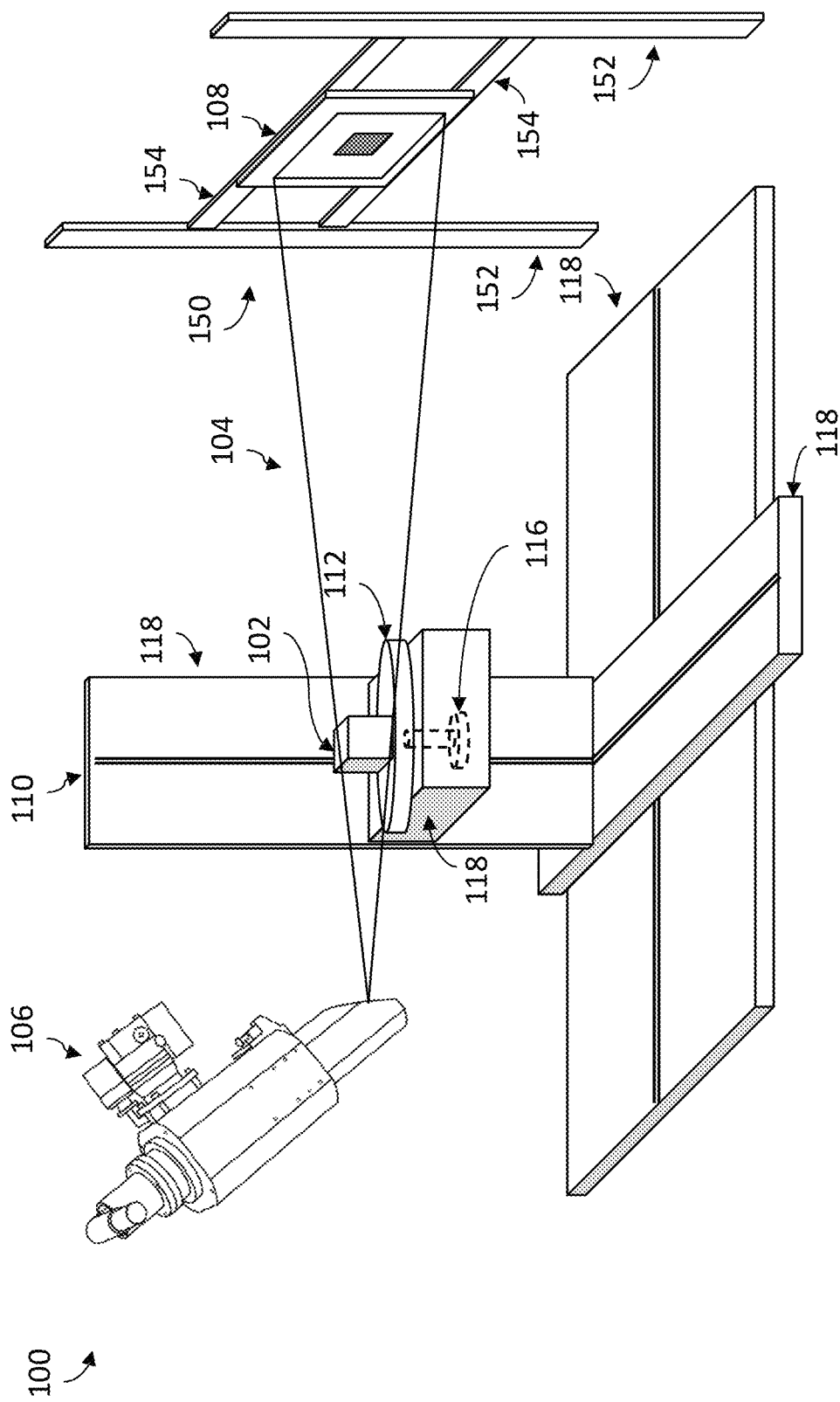
FIG. 1 shows an example of an industrial X-ray radiography system, in accordance with aspects of this disclosure.

In computed tomography (CT) and other industrial radiography applications, spatial resolution is a parameter used to describe the sizes of features capable of being resolved in the resulting radiographic image. Unsharpness is seen in radiography images as blurring, such as around edges of the object-under-inspection. Unsharpness is related to several parameters of the radiography configuration, including geometry, size of the emitter focal spot and factors that affect the focal spot such as emitter voltage, emitter current, emitter wattage. In general, unsharpness increases with an increase in focal spot size and increases with increases in geometric magnification.

In some conventional radiography system designs, the focal spot is set to a specific size and the wattage is limited for the set focal spot size. The focal spot size varies small amounts with changes in emitter voltage, current, and/or wattage. In some other conventional radiography systems, the focal spot size increases as the wattage increases, and the focal spot size of the emitter is somewhat proportional to the emitter wattage. Some conventional radiography systems assume a focal spot size based on the wattage. However, due to assuming the focal spot size, the operator is also required to estimate or predict the operational parameters. As a result of imprecise setting of parameters, conventional systems may produce radiography images that have higher than desired (or higher than acceptable) unsharpness and/or require longer radiography process times to obtain images having an acceptable unsharpness. Furthermore, radiographic emitters can degrade or otherwise become altered over time, causing the relationships between focal spot size and wattage to change. Additionally or alternatively, detector degradation may impact spatial resolution and creating a need for an increase in geometric magnification, which may require corresponding changes in emitter configuration.

Disclosed systems and methods perform measurements of the focal spot size to determine and/or guide selection of one or more parameters of a radiography system to perform a radiography process. By measuring the actual focal spot size, the true unsharpness of a radiographic system can be understood for a given radiography technique or application, thereby allowing for more accurate representations of the blur in the image. In some examples, a radiography system may be populated with measurement data relating emitter wattage, emitter voltage, emitter current, focal spot size in one or more dimensions, two-dimensional and/or three-dimensional spatial resolution, voxel size, pixel pitch, and/or geometric magnification for the radiography system. The stored measurement data may be updated and/or supplemented with measurements taken following installation of the radiographic system.

Disclosed example systems and methods provide a recommendation for one or more radiographic imaging parameters, based on measuring the focal spot of the radiography system, to provide an unsharpness that is less than a predetermined threshold without causing increases in imaging process time associated with reducing unsharpness by significantly more than the threshold. For example, the example systems and methods may try to optimize a balance between unsharpness and imaging process time (e.g., photon count, frames per second, total process time, etc.), by maximizing the wattage while remaining below the threshold unsharpness value. In some examples, the threshold unsharpness corresponds to a pixel or voxel size or a pixel pitch of the radiographic detector, because decreasing blur further below the size of a single pixel may result in undetectable and non-beneficial changes in image quality. However, in other examples in which a sub-pixel spatial resolution is used, the threshold unsharpness (or upper limit of a target unsharpness range) may be less than the pixel pitch of the detector. Image quality is increased as unsharpness is decreased. If the image improves due to changes in imaging parameters, then the focal spot size has been improved for a specific geometric magnification. Disclosed example systems and methods make use of the single-pixel threshold by measuring the focal spot size to determine a specific unsharpness value for a given geometric magnification and wattage.

While example systems and methods are disclosed below with reference to an unsharpness parameter or value, other examples may use similar, equivalent, or related measures such as sharpness or spatial resolution. The terms "unsharpness" and "blur" are used interchangeably herein.

As used herein, the terms "effective pixel pitch" and "voxel size" are used interchangeably.

Disclosed example methods to configure a radiography system having a radiation emitter and a radiation detector involve: analyzing, using processing circuitry, a reference image captured using a first value of a first power parameter for the radiation emitter to determine a value of a focal spot size for the radiation emitter; based on a determined relationship between the first value of the first power parameter and the value of the focal spot size, output an indication of whether a selected value of the first power parameter results in a value of an unsharpness parameter satisfying a threshold unsharpness value; and control the radiography system using the selected power parameter to perform a radiography process to obtain one or more radiographic images that satisfy the threshold unsharpness value.

Some example methods further involve receiving an updated value of the first power parameter, and outputting an indication of whether the updated value of the first power parameter results in the value of the unsharpness parameter satisfying the threshold unsharpness value. Some example methods further involve outputting a recommended change to the value of the first power parameter to cause the value of the first power parameter to result in the value of the unsharpness parameter satisfying the threshold unsharpness value.

Some example methods further involve outputting an indication of whether a detected magnification value results in the value of the unsharpness parameter satisfying a threshold unsharpness value. Some example methods further involve outputting a recommended change to the magnification value to cause the value of the first power parameter to result in the value of the unsharpness parameter satisfying the threshold unsharpness value.

In some example methods, the threshold unsharpness value is based on at least one of a pixel size of the radiation detector or a pixel pitch of the radiation detector. In some example methods, the threshold unsharpness value is set to one of a dimension of a pixel of the radiation detector or a pixel pitch of the radiation detector. In some example methods, the analyzing of the reference image involves analyzing the reference image to determine one or more dimensions of a reference feature based on a predetermined gauge device. Some example methods further involve measuring one or more dimensions of blur in the reference image, and storing the one or more dimensions in a storage device in association with at least one of the first power parameter, a location of the measurement on the reference image, the current focal spot size, a voxel size, an effective pixel pitch, or a magnification parameter.

In some example methods, the radiation emitter includes an X-ray tube and the radiation detector includes a digital X-ray detector. Some example methods further involve determining the value of the unsharpness parameter based on the measured focal spot size and a magnification parameter.

Disclosed example radiography systems include: a user interface; a radiation detector; a radiation emitter configured to emit radiation toward the radiation detector; an object positioner configured to position an object-under-inspection between the radiation detector and the radiation emitter; and a computing device comprising processing circuitry configured to: analyze a reference image captured using a first value of a first power parameter for the radiation emitter to determine a value of a focal spot size for the radiation emitter; based on a determined relationship between the first value of the first power parameter and the value of the focal spot size, output, via the user interface, an indication of whether a selected value of the first power parameter results in a value of an unsharpness parameter satisfying a threshold unsharpness value; and control the radiation emitter using the selected power parameter to perform a radiography process to obtain one or more radiographic images that satisfy the threshold unsharpness value.

In some example radiography systems, the user interface is configured to receiving an updated value of the first power parameter, and the processing circuitry is configured to output an indication of whether the updated value of the first power parameter results in the value of the unsharpness parameter satisfying the threshold unsharpness value. In some example radiography systems, the processing circuitry is configured to output a recommended change to the value of the first power parameter to cause the value of the first power parameter to result in the value of the unsharpness parameter satisfying the threshold unsharpness value.

In some example radiography systems, the processing circuitry is configured to output an indication of whether a detected magnification value results in the value of the unsharpness parameter satisfying a threshold unsharpness value. In some example radiography systems, the processing circuitry is configured to output a recommended change to the magnification value to cause the value of the first power parameter to result in the value of the unsharpness parameter satisfying the threshold unsharpness value.

In some example radiography systems, the threshold unsharpness value is based on at least one of a pixel size of the radiation detector or a pixel pitch of the radiation detector. In some example radiography systems, the threshold unsharpness value is set to one of a dimension of a pixel of the radiation detector or a pixel pitch of the radiation detector. In some example radiography systems, the processing circuitry is configured to analyze the reference image by analyzing the reference image to determine one or more dimensions of a reference feature based on a predetermined gauge device. In some example radiography systems, the processing circuitry is configured to: measure one or more dimensions of blur in the reference image; and store the one or more dimensions in a storage device in association with at least one of the first power parameter, a location of the measurement on the reference image, the current focal spot size, a voxel size, an effective pixel pitch, or a magnification parameter.

FIG. 1 shows an example industrial X-ray radiography system 100. In some examples, the X-ray radiography system 100 may be used to perform non-destructive testing (NDT), digital radiography (DR) scans, computerized tomography (CT) scans, and/or other applications on an object 102. In some examples, the object 102 may be an industrial component and/or an assembly of components (e.g., an engine cast, microchip, bolt, etc.). In some examples, the object 102 may be relatively small, such that a finer, more detailed, higher resolution radiographic imaging process may be useful. While primarily discussed in terms of X-rays for the sake of simplicity, in some examples, the industrial X-ray radiography system 100 discussed herein may use radiation in other wavelengths (e.g., Gamma, Neutron, Terahertz, etc.).

In the example of FIG. 1, the X-ray radiography system 100 directs X-ray radiation 104 from an X-ray emitter 106, through the object 102, to an X-ray detector 108. In some examples, the X-ray emitter 106 may comprise an X-ray tube configured to emit cone or fan shaped X-ray radiation. In some examples, the X-ray emitter 106 may emit X-ray radiation within an energy range of 20 kiloelectron volts (keV) to 15 megaelectron volts (MeV).

In some examples, two dimensional (2D) digital images (e.g., radiographic images, X-ray images, etc.) may be generated based on the X-ray radiation 104 incident on the X-ray detector 108. In some examples, the 2D images may be generated by the X-ray detector 108 itself. In some examples, the 2D images may be generated by the X-ray detector 108 in combination with a computing system in communication with the X-ray detector 108.

In some examples, the 2D images may be constantly captured/acquired by the X-ray detector 108 (e.g., in a free run mode) at a given frame rate, as long as the X-ray detector 108 is powered. However, in some examples, the 2D images may only be fully generated by the X-ray detector 108 (and/or associated computing system(s)) when a scanning/imaging process has been selected and/or is running. Likewise, in some examples, the 2D images may only be saved in permanent (i.e., non-volatile) memory when a scanning/imaging process has been selected and/or is running.

In some examples, the 2D images generated by the X-ray detector 108 (and/or associated computing system(s)) may be combined to form three dimensional (3D) volumes and/or images. In some examples, 2D image slices of the 3D volumes/images may also be formed. While the term "image" is used herein as a shorthand, it should be understood that an "image" may comprise representative data until that data is visually rendered by one or more appropriate components (e.g., a display screen, a graphic processing unit, an X-ray detector 108, etc.).

In some examples, the X-ray detector 108 may comprise a flat panel detector (FDA), a linear diode array (LDA), and/or a lens-coupled scintillation detector. In some examples, the X-ray detector 108 may comprise a fluoroscopy detection system and/or a digital image sensor configured to receive an image indirectly via scintillation. In some examples, the X-ray detector 108 may be implemented using a sensor panel (e.g., a charge coupled device (CCD) panel, a complementary metal-oxide-semiconductor (CMOS) panel, etc.) configured to receive the X-rays directly, and to generate the digital images. In some examples, the X-ray detector 108 may include a scintillation layer/screen that absorbs X-rays and emits visible light photons that are, in turn, detected by a solid-state detector panel (e.g., a CMOS X-ray panel and/or CCD X-ray panel) coupled to the scintillation screen.

In some examples, the X-ray detector 108 (e.g., the solid state detector panel) may include pixels. In some examples, the pixels may correspond to portions of a scintillation screen. In some examples, the size of each pixel may range from tens to hundreds of micrometers. In some examples, the pixel size of the X-ray detector 108 may be in the range of 25 micrometers to 250 micrometers (e.g., 200 micrometers). The pixel pitch refers to the distance from center-to-center of adjacent pixels. Pixel pitch may be the same or different along different directions or axes of the X-ray detector 108.

In some examples, the 2D image captured by the X-ray detector 108 (and/or associated computing system) may contain features finer (e.g., smaller, denser, etc.) than the pixel size of the X-ray detector 108. For example, a computer microchip may have very fine features that are smaller than a pixel. In such examples, it may be useful to use sub-pixel sampling to achieve a higher, more detailed, resolution than might otherwise be possible.

In the example of FIG. 1, the X-ray system 100 includes a detector positioner 150 configured to move the X-ray detector 108 to different detector positions (e.g., for sub-pixel sampling). As shown, the detector positioner 150 includes two parallel pillars 152 connected by two parallel rails 154. As shown the X-ray detector 108 is retained on the rails 154. In some examples, the X-ray detector 108 may be retained on (and/or attached to) the rails 154 by one or more intermediary supports.

As the X-ray detector 108 may be moved by the detector positioner 150, in some examples, the object 102 may be moved by an object positioner 110. In the example of FIG. 1, the object positioner 110 retains the object 102 in the path of the X-ray radiation 104, between the X-ray emitter 106 and detector 108. In some examples, the object positioner 110 may be configured to move the object 102 towards and/or away from the X-ray emitter 106 and/or X-ray detector 108, thereby changing the geometric magnification (defined as the distance between the X-ray emitter 106 and the X-ray detector 108 divided by the distance between the X-ray emitter 106 and the object 102). In some examples, the object positioner 110 may be configured to move and/or rotate the object 102 so that a desired portion and/or orientation of the object 102 is located in the path of the X-ray radiation 104. In some examples, the object positioner 110 may position the object 102 at different angles/orientations with respect to the X-ray emitter 106 and/or X-ray detector 108 in order to obtain 2D images at different orientations, which may then be used to generate one or more three dimensional (3D) images of the object 102.

In the example of FIG. 1, the object positioner 110 includes a rotatable fixture 112 upon which the object 102 is positioned. As shown, the rotatable fixture 112 is a circular plate. As shown, the rotatable fixture 112 is attached to a motorized spindle 116, through which the rotatable fixture 112 may be rotated about an axis defined by the spindle 116. In some examples, one or more alternative and/or additional rotation mechanisms may be provided.

In the example of FIG. 1, the rotatable fixture 112 is supported by a support structure 118. In some examples, the support structure 118 may be configured to translate the rotatable fixture 112 (and/or the object 102) toward and/or away from the X-ray emitter 106 and/or the X-ray detector 108. Additionally the support structure 118 may be configured to translate the rotatable fixture 112 (and/or the object 102) horizontally or vertically in relationship to the emitter 106 and the detector 108. In some examples, the support structure 118 may include one or more actuators configured to impart the translation(s). In some other examples, the X-ray emitter 106 and/or the X-ray detector 108 may be moved with respect to a stationary or moveable fixture and the support structure 118. For example, the X-ray emitter 106 and/or the X-ray detector 108 may be moved toward and/or away from the fixture, upwards and/or downwards with respect to the fixture, rotated around the fixture, and/or otherwise moved and/or reoriented while the fixture remains stationary or is moved and/or reoriented.

While one example object positioner 110 is shown in the example of FIG. 1, in some examples a different object positioner 110 may be used. For example, a robotic object positioner may be used to translate and/or rotate the object 102. Likewise, while shown as a circular plate in the example of FIG. 1, in some examples, the rotatable fixture 112 may instead comprise a different fixture, such as, for example, a clamp, clasp, gripper, and/or other retention mechanism.

Figure 2:
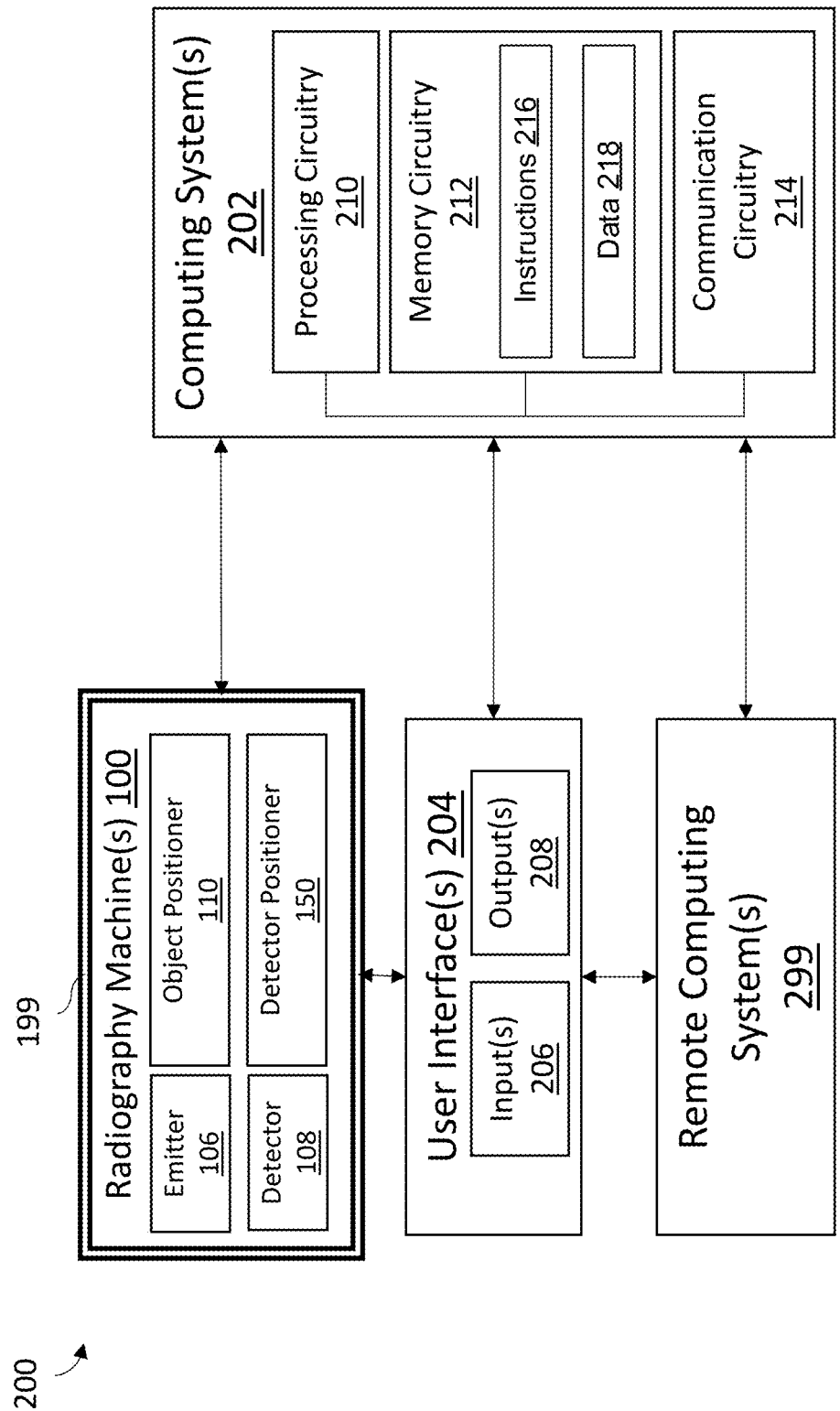
FIG. 2 is a block diagram showing an example X-ray radiography system having the industrial X-ray radiography machine of FIG. 1.

FIG. 2 shows an example of an X-ray radiography system 200 that includes an X-ray radiography system 100, such as, for example, the X-ray radiography system 100 shown in FIG. 1. As shown, the X-ray radiography system 200 also includes a computing system 202, a user interface (UI) 204, and a remote computing system 299. While only one X-ray radiography system 100, computing system 202, UI 204, and remote computing system 299 are shown in the example of FIG. 2, in some examples the X-ray radiography system 200 may include several X-ray radiography systems 100, computing systems 202, UIs 204, and/or remote computing systems 299.

In the example of FIG. 2, the X-ray radiography system 100 has an emitter 106, detector 108, detector positioner 150, and object positioner 110 enclosed within a housing 199. As shown, the X-ray radiography system 100 is connected to and/or in communication with the computing system(s) 202 and UI(s) 204. In some examples, the X-ray radiography system 100 may also be in electrical communication with the remote computing system(s) 299. In some examples, the communications and/or connections may be electrical, electromagnetic, wired, and/or wireless.

In the example of FIG. 2, the UI 204 includes one or more input devices 206 and/or output devices 208. In some examples, the one or more input devices 206 may comprise one or more touch screens, mice, keyboards, buttons, switches, slides, knobs, microphones, dials, and/or other electromechanical input devices. In some examples, the one or more output devices 208 may comprise one or more display screens, speakers, lights, haptic devices, and/or other devices. In some examples, a user may provide input to, and/or receive output from, the X-ray radiography machine(s) 100, computing system(s) 202, and/or remote computing system(s) 299 via the UI(s) 204.

In some examples, the UI(s) 204 may be part of the computing system 202. In some examples, the computing system 202 may implement one or more controllers of the X-ray radiography machine(s) 100. In some examples, the computing system 202 together with the UI(s) 204 may comprise an image acquisition system of the X-ray radiography system 200. In some examples, the remote computing system(s) 299 may be similar or identical to the computing system 202.

In the example of FIG. 2, the computing system 202 is in (e.g., electrical) communication with the X-ray radiography machine(s) 100, UI(s) 204, and remote computing system(s) 299. In some examples, the communication may be direct communication (e.g., through a wired and/or wireless medium) or indirect communication, such as, for example, through one or more wired and/or wireless networks (e.g., local and/or wide area networks). As shown, the computing system 202 includes processing circuitry 210, memory circuitry 212, and communication circuitry 214 interconnected with one another via a common electrical bus.

In some examples, the processing circuitry 210 may comprise one or more processors. In some examples, the communication circuitry 214 may include one or more wireless adapters, wireless cards, cable adapters, wire adapters, radio frequency (RF) devices, wireless communication devices, Bluetooth devices, IEEE 802.11-compliant devices, WiFi devices, cellular devices, GPS devices, Ethernet ports, network ports, lightning cable ports, cable ports, etc. In some examples, the communication circuitry 214 may be configured to facilitate communication via one or more wired media and/or protocols (e.g., Ethernet cable(s), universal serial bus cable(s), etc.) and/or wireless mediums and/or protocols (e.g., near field communication (NFC), ultra high frequency radio waves (commonly known as Bluetooth), IEEE 802.11x, Zigbee, HART, LTE, Z-Wave, WirelessHD, WiGig, etc.).

In the example of FIG. 2, the memory circuitry 212 comprises and/or stores one or more focal spot measurement processes and/or imaging processes. In some examples, the one or more focal spot measurement processes and/or imaging processes are implemented via machine readable (and/or processor executable) instructions 216 stored in memory circuitry 212 and/or executed by the processing circuitry 210. In some examples, the one or more focal spot measurement processes and/or imaging processes are executed as part of a larger scanning and/or imaging process of the X-ray radiography system 200. The example memory circuitry 212 may further include data, such as reference tables or lookup tables, containing measurement data.

The example radiography system 100 of FIGS. 1 and 2 performs a focal spot measurement process to measure the focal spot for a configuration of the radiography system 100. The focal spot measurement process may be performed manually or automatically. The configuration may involve a particular wattage for the emitter 106 and/or a geometric magnification. The focal spot measurement process may be performed periodically (e.g., every day or other set period), aperiodically, at scheduled times, on demand, in response to predetermined criteria (e.g., prior to an imaging process), and/or at any other times.

To measure the focal spot size, a reference image is taken using a known reference object having predetermined dimensions. For example, standard reference gauge devices, such as a tungsten wire crosshair or circular or cylindrical plate, have predetermined dimensions which can be used, in conjunction with the geometry of the emitter 106, detector 108, and the position of the reference gauge device as the object 102, to measure the focal spot size via measurement of the unsharpness in the reference image. The reference image may be captured at one or more predetermined reference positions, which may involve predetermined distances between the emitter 106, the detector 108, and/or the object 102. The reference image may be taken as a live image, and/or may be based on a previously captured image (e.g., an image captured using the same power parameter(s)).

Figure 3:
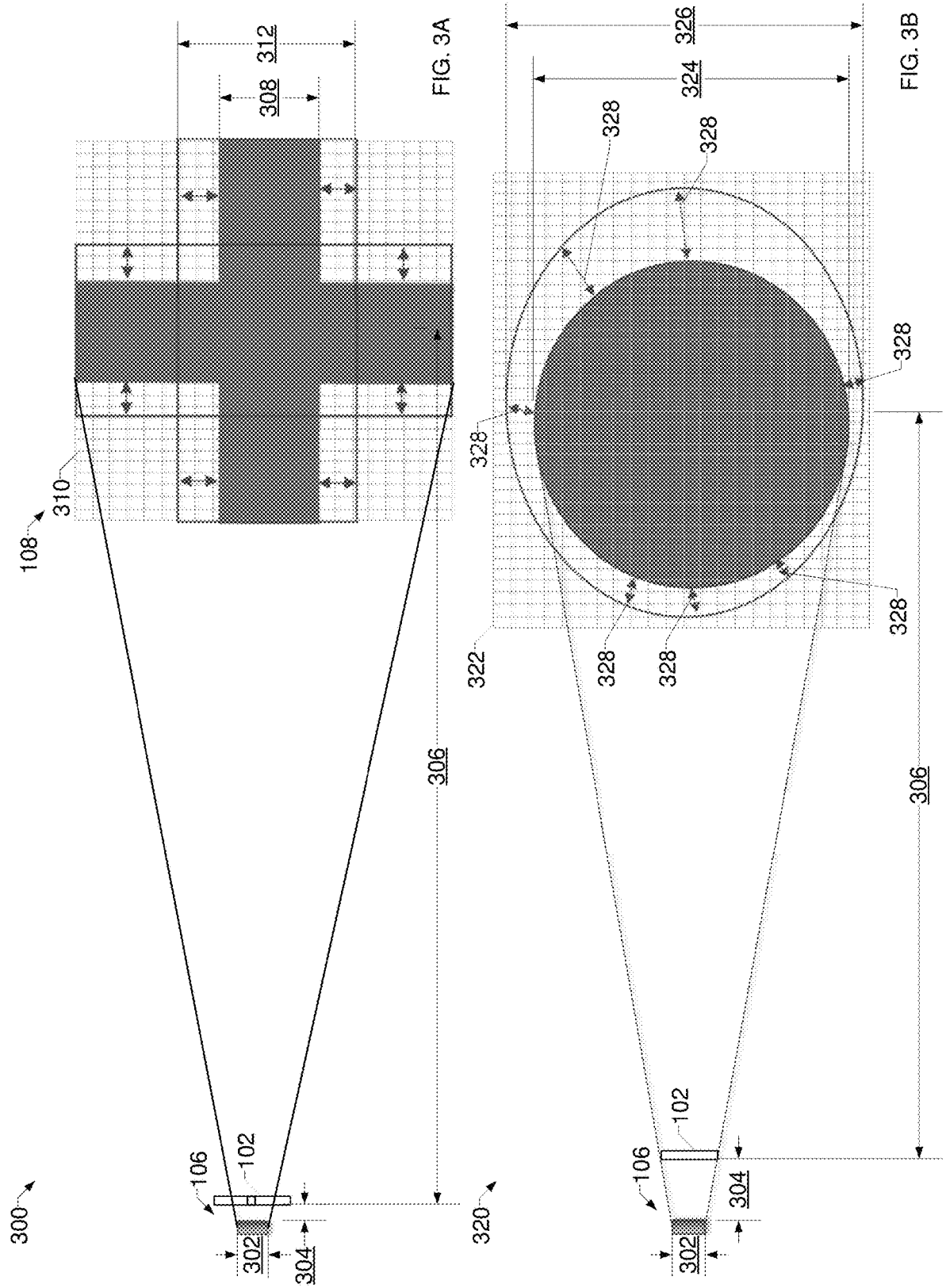
FIGS. 3A and 3B illustrate examples of focal spot measurement configurations that may be implemented using the radiography system of FIGS. 1 and 2 to measure a focal spot size using configured parameters.

FIG. 3A illustrates an example focal spot measurement configuration 300 that may be implemented using the radiography system 100 of FIGS. 1 and 2 to measure a focal spot size 302 using configured parameters. The configuration 300 includes the emitter 106, the detector 108 placed a first distance 304 from the emitter 106, and the object 102 placed a second distance 306 from the emitter 106. The resulting geometric magnification of the configuration 300 is the ratio of the first distance 304 to the second distance 306 (e.g., as the object 102 approaches the emitter 106, the geometric magnification increases).

Based on the distances 304, 306 and the predetermined dimensions of the object 102 (e.g., a tungsten wire crosshair), the radiography system 100 determines an expected size 308 of the object 102 produced in the reference image 310. The example radiography system 100 analyzes the reference image 310 to determine applicable dimensions of a reference feature based on the predetermined dimensions of the object 102. For example, the dimensions may include one or more dimensions of the object 102 in the image 310 and/or one or more dimensions of blur present in the image 310. The radiography system 100 further determines an observed size 312 of the object 102 produced in the reference image. The blur is then determined based on the difference between the observed size 312 and the expected size 308. The radiography system 100 may then calculate the focal spot size based on the measured unsharpness (Ug) using, for example, common industry accepted formulas for measuring unsharpness (e.g., ASTM E2903, ASTM E1165, etc.).

FIG. 3B illustrates another example focal spot measurement configuration 320 that may be implemented using the radiography system 100 of FIGS. 1 and 2 to measure a focal spot size using configured parameters. The example configuration 320 is similar to the configuration 300 of FIG. 3A. However, the example object 102 is a circular or cylindrical plate, or spherical object, which results in a different size shape of reference image 322.

The example radiography system 100 of FIG. 1 determines an expected size 324 of the object in the reference image 322 (e.g., based on the geometry) and the measured size 326 of the object. The radiography system 100 then determines the measured focal spot size based on the measured blur. Because the blur in the reference image 322 of FIG. 3B is non-uniform, the radiography system 100 may determine the blur as an average blur or other filtered value, based on samples 328 taken around the periphery of the object in the reference image and/or based on fitting a function to the blur and determining the average or maximum blur value, or other filtered blur value. The radiography system 100 may then calculate the focal spot size and shape based on the measured unsharpness (Ug). For example, when a circular or spherical object is imaged, the radiography system 100 may calculate measurements of the focal spot size and shape in multiple dimensions. The shape of the focal spot (e.g., the size in 2 or more directions) allows the radiography system 100 to select the geometric magnification and/or wattage for a given application to avoid exceeding the unsharpness threshold in more than one direction. While some examples disclosed herein are discussed with reference to one dimension, any of the example systems and methods may be adapted to measure and configure for multiple dimensions of the focal spot.

Figure 4:
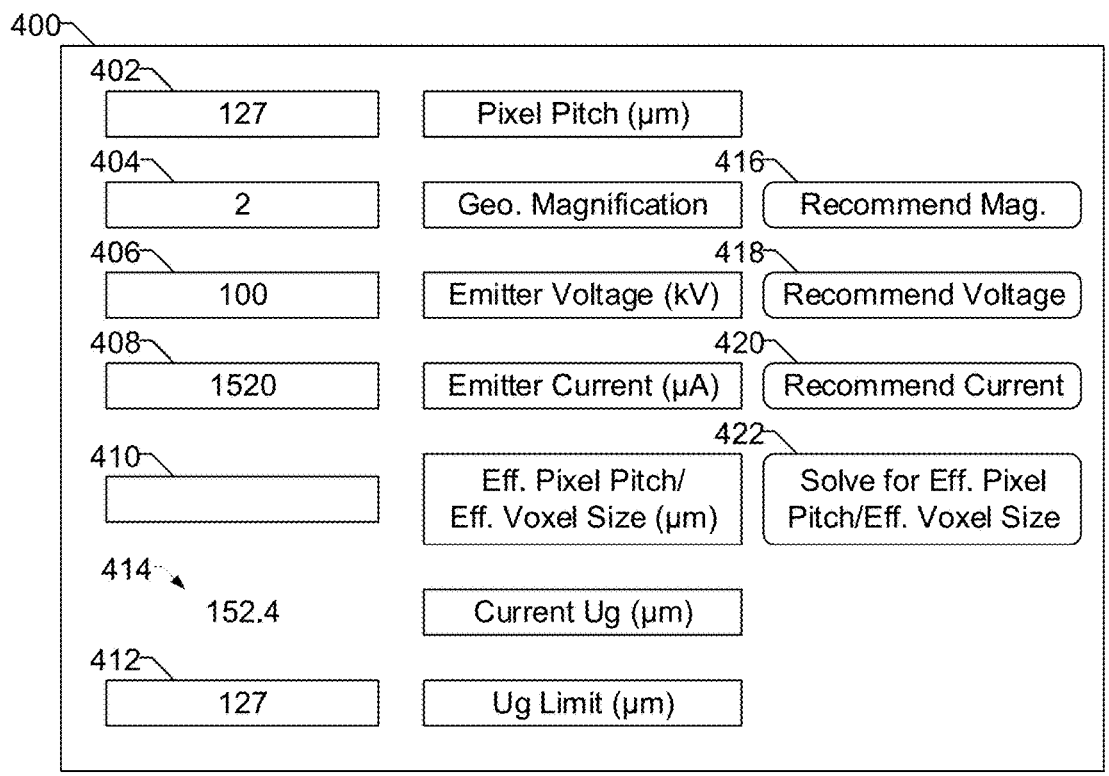
FIG. 4 illustrates an example user interface that may be implemented using the radiography system of FIGS. 1 and 2.

FIG. 4 illustrates an example user interface 400 that may be implemented using the radiography system 100 (e.g., the user interface(s) 204) of FIGS. 1 and 2. The example user interface 400 includes a pixel pitch input 402, a geometric magnification input 404, an emitter voltage input 406, an emitter current input 408, a voxel size input 410, and an unsharpness limit value input 412. The example interface 400 further includes a calculated current unsharpness value output 414.

Any of the example inputs 402-412 may also be selected to be outputs for recommended values based on other ones of the inputs 402-412. After the focal spot size has been measured, the example radiography system 100 may recommend or determine one or more imaging parameters based on one or more input parameters. For example, if the operator inputs (or configures) a particular geometric magnification via the geometric magnification input 404, the radiography system 100 may set or recommend a wattage (e.g., a voltage and/or current) of the emitter 106 to result in an unsharpness value Ug that is less than a threshold unsharpness (e.g., less than the width of 1 pixel, less than the pixel pitch). For example, the interface 400 may display the recommended wattage, voltage, and/or current via displaying values in the voltage input 406 and/or current input 408 fields.

Additionally or alternatively, if the operator inputs (or configures) a particular wattage for the emitter 106 (e.g., via the emitter voltage input 406 and/or the emitter current input 408), the radiography system 100 may set or recommend a geometric magnification (e.g., a physical configuration of the emitter 106, detector 108, and object 102) to achieve an unsharpness value Ug that is less than the threshold unsharpness. For example, the interface 400 may display the recommended geometric magnification via displaying values in the geometric magnification field 404. In still other examples, the operator may specify any of a voxel size limit (e.g., a specific voxel size, a minimum voxel size, a maximum voxel size), a spatial resolution limit (e.g., a minimum spatial resolution), an effective pixel pitch, and/or any other related parameter(s). Based on the requirements or limits that are input, the radiography system 100 may determine any of the focal spot size, wattage, voltage, current, geometric magnification, and/or any other parameters and/or configurations for performing a radiographic imaging process according to the input parameters.

The example interface 400 further includes buttons (or other input devices) which permit the operator to specify which of one or more parameters the operator desires to receive a recommended value. For example, the interface 400 includes a "Recommend Magnification" button 416 to cause the radiography system 100 to determine a geometric magnification value (e.g., based on the pixel pitch 402, the emitter voltage 406, the emitter current 408, and the unsharpness limit 412, the effective pixel pitch or voxel size 410, and/or a determined focal spot size). The interface 400 further includes "Recommend Voltage" and "Recommend Current" buttons 418, 420 to cause the radiography system 100 to determine voltage and/or current values for the emitter 106 (e.g., based on the pixel pitch 402, the geometric magnification 404, the effective pixel pitch or voxel size 410, and the unsharpness limit 412, and/or a determined focal spot size).

The example interface 400 further includes a "Solve for Effective Pixel Pitch/Effective Voxel Size" button 422, which causes the radiography system 100 to determine a set of parameters (e.g., geometric magnification, emitter voltage, emitter current) for a specified voxel size input 410 and unsharpness limit 412 (e.g., based on pixel pitch 402). For example, if the operator specifies a 40 micron voxel requirement for a given radiography process, the radiography system 100 determines the required geometric magnification based on the pixel pitch and the voxel size (e.g., Geometric Magnification=Pixel Pitch/Voxel Size). Using the geometric magnification, the radiography system 100 may then determine the wattage based on the measured focal spot size and the determined geometric magnification.

In some examples, the radiography system 100 stores data 218 (e.g., a reference table, lookup table, or equivalent function) in a storage device (e.g., the memory circuitry 212 of FIG. 2), which relates the emitter wattage, voltage, current, geometric magnification, pixel size, pixel pitch, voxel size, focal spot size, and/or any other parameters to unsharpness. The reference table may be pre-populated using data obtained by the manufacturer, by the installer, by maintenance personnel, and/or by the operator, during or after manufacturing and/or during or after installation of the radiography system 100. Additionally or alternatively, the radiography system 100 may supplemental or update the reference table based on subsequent focal spot measurements.

The example radiography system 100 references the reference table to determine radiography parameters based on input parameters. For example, the reference table may be used when performing a focal spot measurement is not desired by the operator prior to a radiography process, and/or within a defined time window following performance of a focal spot measurement. Table 1 below illustrates a portion of an example reference table that may be stored in the memory circuitry 212, referenced to determine parameters, and/or updated.

values. A reference set of values 502 corresponds to a 1 W/μm of focal spot size default, or assumed, value. A first set of observed focal spot size values 504 are measured at a first emitter voltage (X kV), and a second set of observed focal spot size values are measured at a second emitter voltage (Y kV). The data may include additional voltages and/or may be measured for multiple dimensions of the detector 108.

As the radiography system 100 performs focal spot measurements, the radiography system 100 may add data points to the observed values 504, 506. In some examples, the radiography system 100 replaces existing data points with updated data points if the newer data points have the same emitter wattage.

In some examples, instead of measuring an absolute focal spot size, the stored values (e.g., the reference table above, the values 504, 506, etc.) may be used to determine adjustments to a current configuration. For example, if a particular emitter wattage corresponds to a measured unsharpness value above the unsharpness threshold or significantly below the unsharpness threshold, the radiography system 100 may determine an increment or decrement in wattage based on the values in the table or graph 500 to achieve the desired unsharpness (e.g., a corresponding focal spot size to achieve the unsharpness).

By storing and updating the data, the radiography system 100 may characterize data points and use machine learning algorithms to identify trends, degradation of the radiography system 100 (e.g., degradation of the emitter 106 and/or the detector 108), and/or any other changes to the radiography system 100 over time. For example, the radiography system 100 may identify thresholds of normal focal spot sizes at different wattage values, and/or upper and/or lower control limits to identify fluctuations outside of normal ranges. Additionally or alternatively, the machine learning algorithms may learn to adjust values and/or limits over time and/or over the life of the system, to detect and/or predict changes to the imaging system and resulting effects on the image quality. These potential effects could be accepted by the operator to enable system learning based off those data points. If the data points are deemed to be outside of acceptable ranges (e.g., based on determined thresholds) the operator could be provided options to perform a correction of hardware and/or imaging setup.

TABLE 1

Example Reference Table

| Emitter Voltage (kV) | Power (W) | Focal Spot Size (μm) | Geo. Magnification (at Ug-Focal Measurement location) | Unsharpness (μm) | Detector Pixel Pitch/ Max Ug (μm) | Effective Pixel Pitch/ Voxel (μm) | Geo. Magnification (Calc.) |
|---|---|---|---|---|---|---|---|
| 120 | 5 | 12 | 100 | 1188 | 127 | 11 | 11.5 |
| 225 | 10 | 19 | 100 | 1881 | 127 | 16.5 | 7.7 |
| 90 | 15 | 23 | 100 | 2277 | 127 | 19.5 | 6.5 |
| 100 | 20 | 26 | 100 | 2574 | 127 | 22 | 5.8 |
| 150 | 25 | 28 | 100 | 2772 | 127 | 23 | 5.5 |
| 220 | 30 | 35 | 100 | 3465 | 127 | 28 | 4.6 |
| 180 | 40 | 54 | 100 | 5346 | 127 | 38.5 | 3.3 |
| 80 | 50 | 85 | 100 | 8415 | 127 | 53 | 2.4 |

Figure 5:
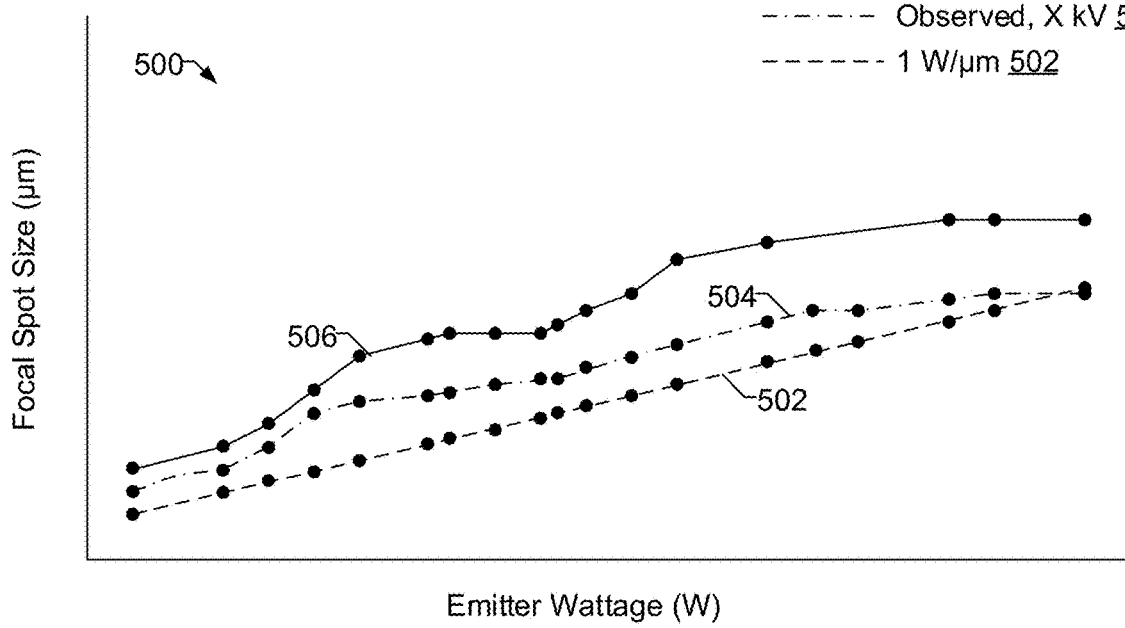
FIG. 5 is a graph representative of example stored focal spot data that may be used to determine a focal spot based on a configured wattage.
Figure 6:
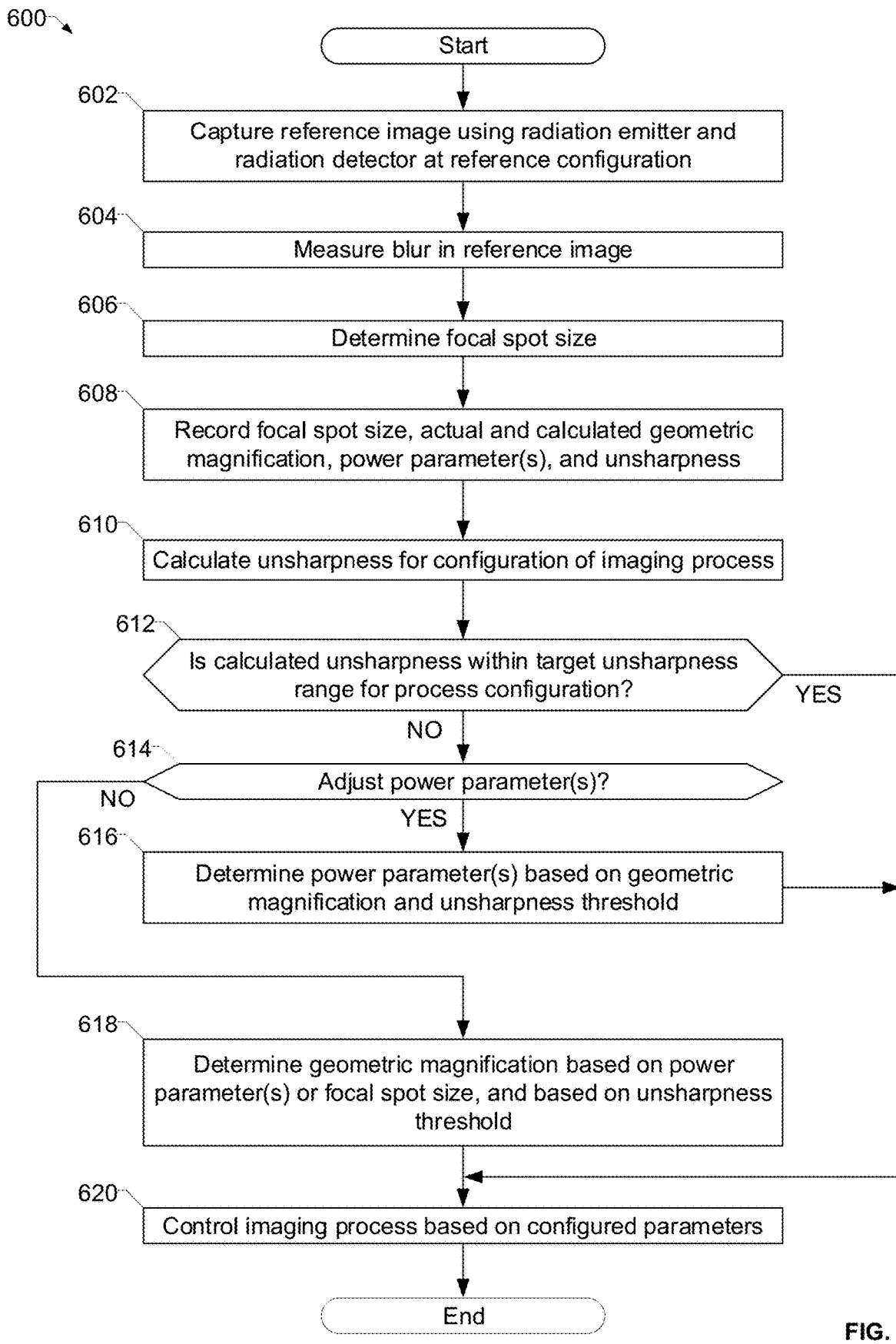
FIG. 6 is a flowchart representative of example machine readable instructions which may be implemented by the example X-ray radiography system of FIGS. 1 and 2 to determine imaging parameters for a radiography process based on a measured focal spot.

FIG. 5 is a graph 500 representative of example stored focal spot data that may be used to determine a focal spot based on a configured wattage. The graph 500 depicts a series of focal spot sizes corresponding to emitter wattage FIG. 6 is a flowchart representative of example machine readable instructions 600 which may be implemented by the example X-ray radiography system 100 of FIGS. 1 and 2 to determine imaging parameters for a radiography process based on a measured focal spot. The example instructions 600 may be stored on a storage device (e.g., the memory circuitry 212 of FIG. 2) and executed by processing circuitry (e.g., the processing circuitry 210 of FIG. 2).

At block 602, the X-ray detector 108 captures a reference image (e.g., the reference image 310 of FIG. 3A) at a reference configuration. For example, the reference configuration may involve a predetermined arrangement of the radiation emitter 106, a reference object 102 under inspection, and an X-ray detector 108. The predetermined arrangement may have been previously measured as a preferred arrangement to achieve an accurate measurement of blur and/or focal spot size.

At block 604, the processing circuitry 210 measures blur in the reference image 310. For example, the processing circuitry 210 may calculate an expected size 308 of the object in the reference image 310 and measure the actual size 312 of the object in the image. The processing circuitry 210 then determines the blur as half of the difference between the expected size 308 and actual size 312. The blur may be measured in multiple dimensions. At block 606, the processing circuitry 210 determines the focal spot size based on the measured blur.

At block 608, the processing circuitry 210 records the focal spot size, actual geometric magnification, calculated geometric magnification, emitter voltage, power parameter(s), and unsharpness (e.g., in a reference table). For example, in addition to recording the geometric magnification used to capture the reference image, the processing circuitry 210 may calculate and store a geometric magnification at which the determined focal spot size would obtain a predetermined unsharpness threshold. The recorded data may be used to update the reference table with current data.

At block 610, the processing circuitry 210 calculates the unsharpness for a configuration of an imaging process to be performed. The configuration of the imaging process may be the same as or different than the reference configuration. For example, the arrangement may change while using the same emitter wattage parameter, resulting in a different geometric magnification and a different unsharpness.

At block 612, the processing circuitry 210 determines whether the calculated unsharpness is within a target unsharpness range for the process configuration. For example, the target unsharpness range may be equivalent to, or based on, a pixel size or a pixel pitch, to cause the processing circuitry 210 to determine whether the unsharpness is less than the equivalent of one pixel. In other examples, the calculated unsharpness may be compared to a voxel size. However, any other desired threshold value may be used.

In some examples, the processing circuitry 210 may determine in block 612 whether the calculated unsharpness is below an upper unsharpness threshold and/or above a lower unsharpness threshold. In some examples, the lower unsharpness threshold is determined as a threshold slightly (e.g., a predetermined amount or percentage of the threshold) below the upper unsharpness threshold, to thereby avoid an unnecessarily long process time to achieve effectively the same image quality.

If the calculated unsharpness is not within the target unsharpness range for the process configuration (block 612), at block 614 the processing circuitry 210 determines whether to adjust (e.g., correct) a power parameter (e.g., wattage, voltage, current). For example, the processing circuitry 210 may determine whether the geometric magnification is fixed and/or whether the operator has requested a recommendation for the power parameter(s). In some examples, the processing circuitry 210 determines whether to adjust (e.g., correct) the geometric magnification parameter instead of the power parameter. For example, the processing circuitry 210 may determine whether the power parameters are fixed and/or whether the operator has requested a recommendation for the magnification.

If the power parameter is to be adjusted (block 614), at block 616 the processing circuitry 210 determines one or more power parameters based on the geometric magnification and the unsharpness threshold. For example, the processing circuitry 210 may look up a wattage, a voltage, and/or a current in a reference table (e.g., the data 218 of FIG. 2) based on the geometric magnification and unsharpness threshold. In some examples, the determination may include interpolation between sets of data points in the table. The determination may further involve outputting an indication that the selected value(s) of the power parameter(s) result in the value of an unsharpness parameter satisfying the threshold unsharpness.

If the power parameter is not to be adjusted (block 614), at block 618 the processing circuitry 210 determines the geometric magnification based on one or more power parameters and the unsharpness threshold. For example, the processing circuitry 210 may look up a geometric magnification in a reference table (e.g., the data 218 of FIG. 2) based on the wattage, voltage, and/or current, and the unsharpness threshold. In some examples, the determination may include interpolation between sets of data points in the table. The determination may further involve outputting an indication that the selected value of the geometric magnification results in the value of an unsharpness parameter satisfying the threshold unsharpness.

After determining the geometric magnification correction (block 618), after determining the power parameter correction(s) (block 616), if none of the parameters are to be corrected (block 618), and/or if the calculated unsharpness is within the target unsharpness range (block 612), at block 620 the processing circuitry 210 controls the imaging process based on the configured parameters. For example, the processing circuitry 210 controls the emitter 106 and detector 108 to generate one or more 2D and/or radiographs for 3D data (e.g., 3D CT scans, etc.) using the parameters recommended via blocks 602-618 based on the measured focal spot size. The example instructions 600 then end.

Figure 7A:
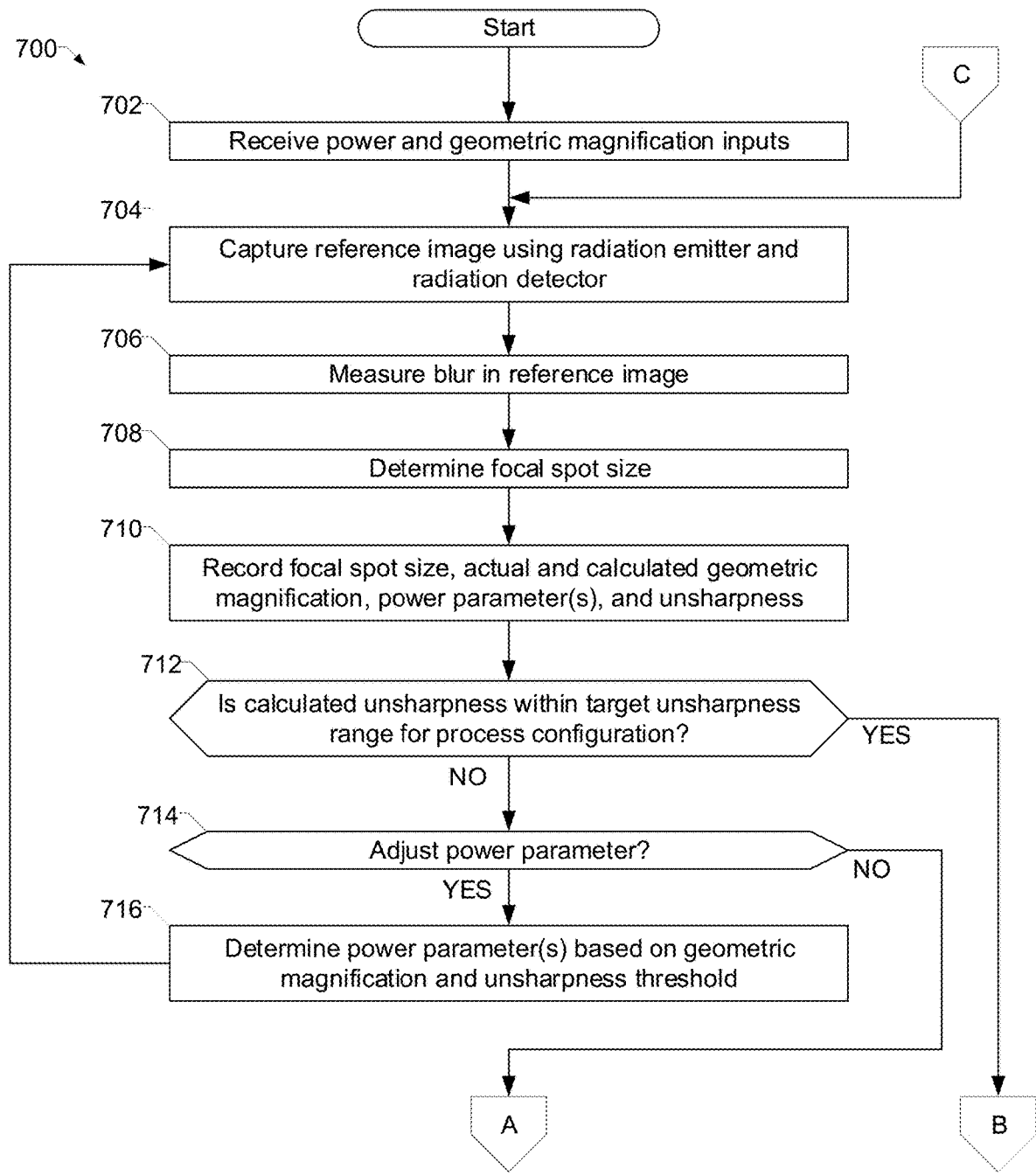
FIGS. 7A and 7B illustrate a flowchart representative of other example machine readable instructions which may be implemented by the example X-ray radiography system of FIGS. 1 and 2 to determine imaging parameters for a radiography process based on a measured focal spot.
Figure 7B:
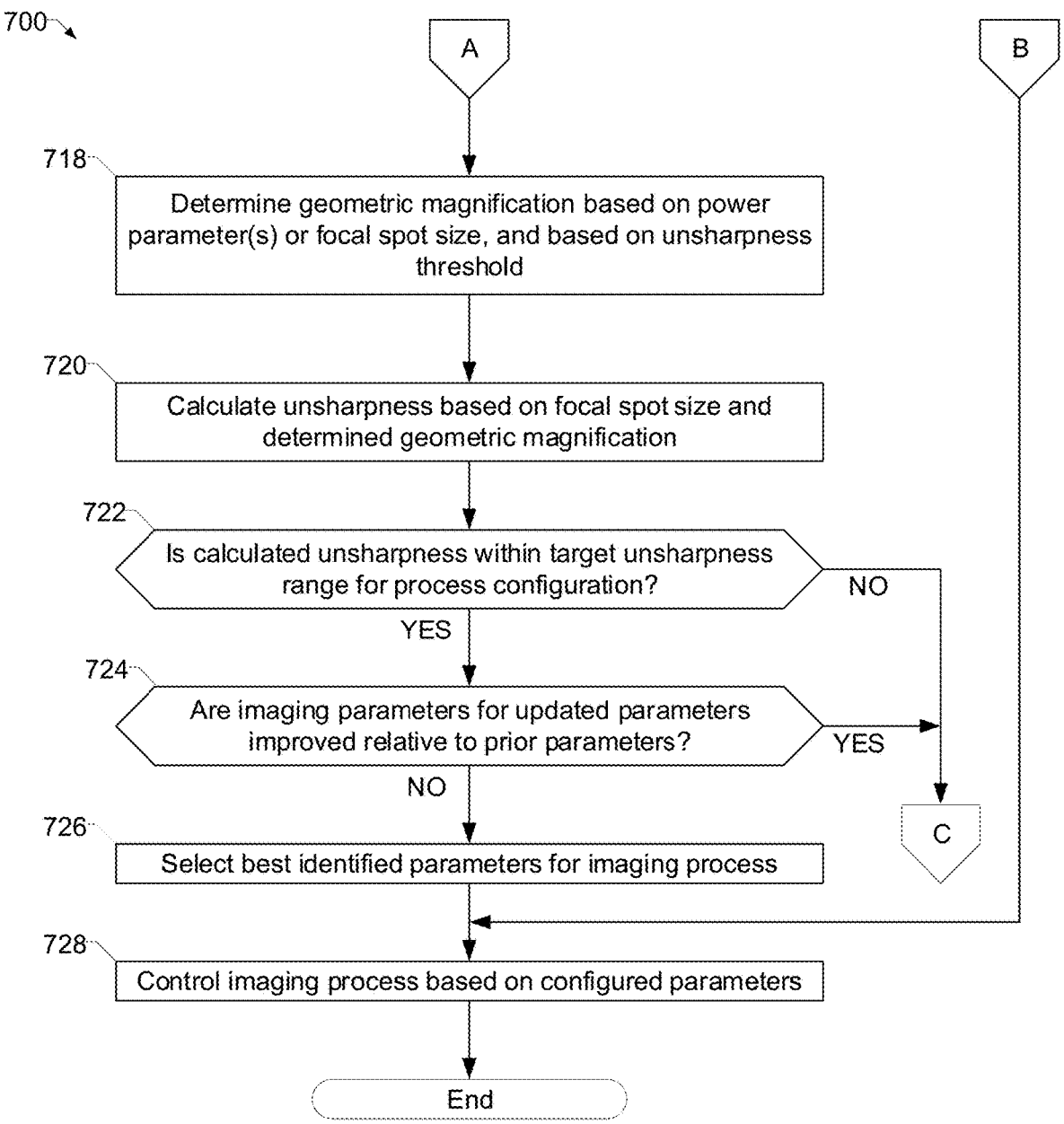

FIGS. 7A and 7B illustrate a flowchart 700 representative of other example machine readable instructions which may be implemented by the example X-ray radiography system of FIGS. 1 and 2 to determine imaging parameters for a radiography process based on a measured focal spot. The example instructions 700 may be stored on a storage device (e.g., the memory circuitry 212 of FIG. 2) and executed by processing circuitry (e.g., the processing circuitry 210 of FIG. 2).

At block 702, the processing circuitry 210 receives (e.g., via the user interface 214, 400 of FIGS. 2 and 4) power parameter and geometric magnification inputs. For example, the operator may input the wattage, voltage, and/or current, and the geometric magnification, into the user interface 400. In other examples, the power parameter and geometric magnification inputs may be automatically received (e.g., from a remote computing device, a data storage device) in association with an object 102 to be inspected with the system 100.

At block 704, the X-ray detector 108 captures a reference image (e.g., the reference image 310 of FIG. 3A) at a reference configuration, which may include the received power and geometric magnification inputs or a predetermined power and geometric magnification. For example, the reference configuration may involve a predetermined arrangement of the radiation emitter 106, a reference object 102 under inspection, and an X-ray detector 108. The predetermined arrangement may have been previously measured as a preferred arrangement to achieve an accurate measurement of blur and/or focal spot size.

At block 706, the processing circuitry 210 measures blur in the reference image 310. For example, the processing circuitry 210 may calculate an expected size 308 of the object in the reference image 310 and measure the actual size 312 of the object in the image. The processing circuitry 210 then determines the blur as half of the difference between the expected size 308 and actual size 312. The blur may be measured in multiple dimensions. At block 708, the processing circuitry 210 determines the focal spot size based on the measured blur.

At block 710, the processing circuitry 210 records the focal spot size, actual geometric magnification, calculated geometric magnification, power parameter(s), and unsharpness (e.g., in a reference table). For example, in addition to recording the geometric magnification used to capture the reference image, the processing circuitry 210 may calculate and store a geometric magnification at which the determined focal spot size to obtain a predetermined unsharpness threshold. The actual geometric magnification and power parameter(s) may be the received geometric magnification and power parameter inputs if used to generate the reference image 310. The recorded data may be used to update the reference table with current data.

At block 712, the processing circuitry 210 determines whether the measured unsharpness is within a target unsharpness range for the process configuration. For example, an upper threshold of the target unsharpness range may be equivalent to, or based on, a pixel size or a pixel pitch, to cause the processing circuitry 210 to determine whether the unsharpness is less than the equivalent of one pixel. In other examples, the calculated unsharpness may be compared to an voxel size. However, any other desired threshold value may be used.

In some examples, the processing circuitry 210 may determine in block 712 whether the calculated unsharpness is below an upper unsharpness threshold and/or above a lower unsharpness threshold. In some examples, the lower unsharpness threshold is determined as a threshold slightly (e.g., a predetermined amount or percentage of the threshold) below the upper unsharpness threshold, to thereby avoid an unnecessarily long process time to achieve effectively the same image quality.

If the calculated unsharpness is not within the target unsharpness range for the process configuration (block 712), at block 714 the processing circuitry 210 determines whether to adjust (e.g., correct) power parameter(s) (e.g., wattage, voltage, current). For example, the processing circuitry 210 may determine whether the geometric magnification is fixed and/or whether the operator has requested a recommendation for the power parameter(s). In some examples, the processing circuitry 210 determines whether to adjust (e.g., correct) the geometric magnification parameter instead of the power parameter(s). For example, the processing circuitry 210 may determine whether the power parameter(s) are fixed and/or whether the operator has requested a recommendation for the magnification.

If the power parameter is to be adjusted (block 714), at block 716 the processing circuitry 210 determines one or more power parameters based on the geometric magnification and the unsharpness threshold. For example, the processing circuitry 210 may look up a wattage, a voltage, and/or a current in a reference table (e.g., the data 218 of FIG. 2) based on the geometric magnification and unsharpness threshold. In some examples, the determination may include interpolation between sets of data points in the table. The determination may further involve outputting an indication that the selected value(s) of the power parameter(s) result in the value of an unsharpness parameter satisfying the threshold unsharpness. Control then returns to block 704 to iterate the focal spot measurement and comparison of unsharpness to the threshold.

With reference to FIG. 7B, if the power parameter(s) are not to be adjusted (block 714), at block 718 the processing circuitry 210 determines the geometric magnification based on one or more power parameters and the unsharpness threshold. For example, the processing circuitry 210 may look up a geometric magnification in a reference table (e.g., the data 218 of FIG. 2) based on the wattage, voltage, and/or current, and the unsharpness threshold. In some examples, the determination may include interpolation between sets of data points in the table. The determination may further involve outputting an indication that the selected value of the geometric magnification results in the value of an unsharpness parameter satisfying the threshold unsharpness.

At block 720, the processing circuitry 210 calculates an updated unsharpness value based on the measured focal spot size and the determined geometric magnification.

At block 722, the processing circuitry 210 determines whether the calculated unsharpness is within the target unsharpness range for the process configuration. Block 722 may be identical to, similar to, or different than block 712. If the calculated unsharpness is within the target unsharpness range (block 722), at block 724 the processing circuitry 210 determines whether the imaging parameters for the updated parameters and/or configuration are improved relative to the prior parameters. For example, the processing circuitry 210 may determine whether the imaging process time is higher or lower than a previous iteration while remaining below the threshold unsharpness. If the imaging parameter are improved (block 724), or if the calculated unsharpness is not less than the threshold unsharpness (block 722), control returns to block 704 to iterate the focal spot measurement (e.g., with a different configuration) to improve the parameters.

In this manner, the processing circuitry 210 may iterate parameters to obtain acceptable, improved, or optimal parameters and configuration for a desired radiography process.

If the imaging parameters are not improved (block 724), at block 726 the processing circuitry 210 selects the best identified parameters for the imaging process. The parameters may, for example, be stored in the reference table for each calculated unsharpness value and configuration.

If the calculated unsharpness is less than the threshold unsharpness (block 712) or if the power parameter(s) and geometric magnification are not to be adjusted (block 718), or after selecting the best identified parameters (block 726), at block 728 the processing circuitry 210 controls the imaging process based on the configured parameters. For example, the processing circuitry 210 controls the emitter 106 and detector 108 to generate one or more 2D and/or radiographs for 3D data (e.g., 3D CT scans, etc.) using the parameters recommended via blocks 702-726 based on the measured focal spot size. The example instructions 700 then end.

Figure 8:
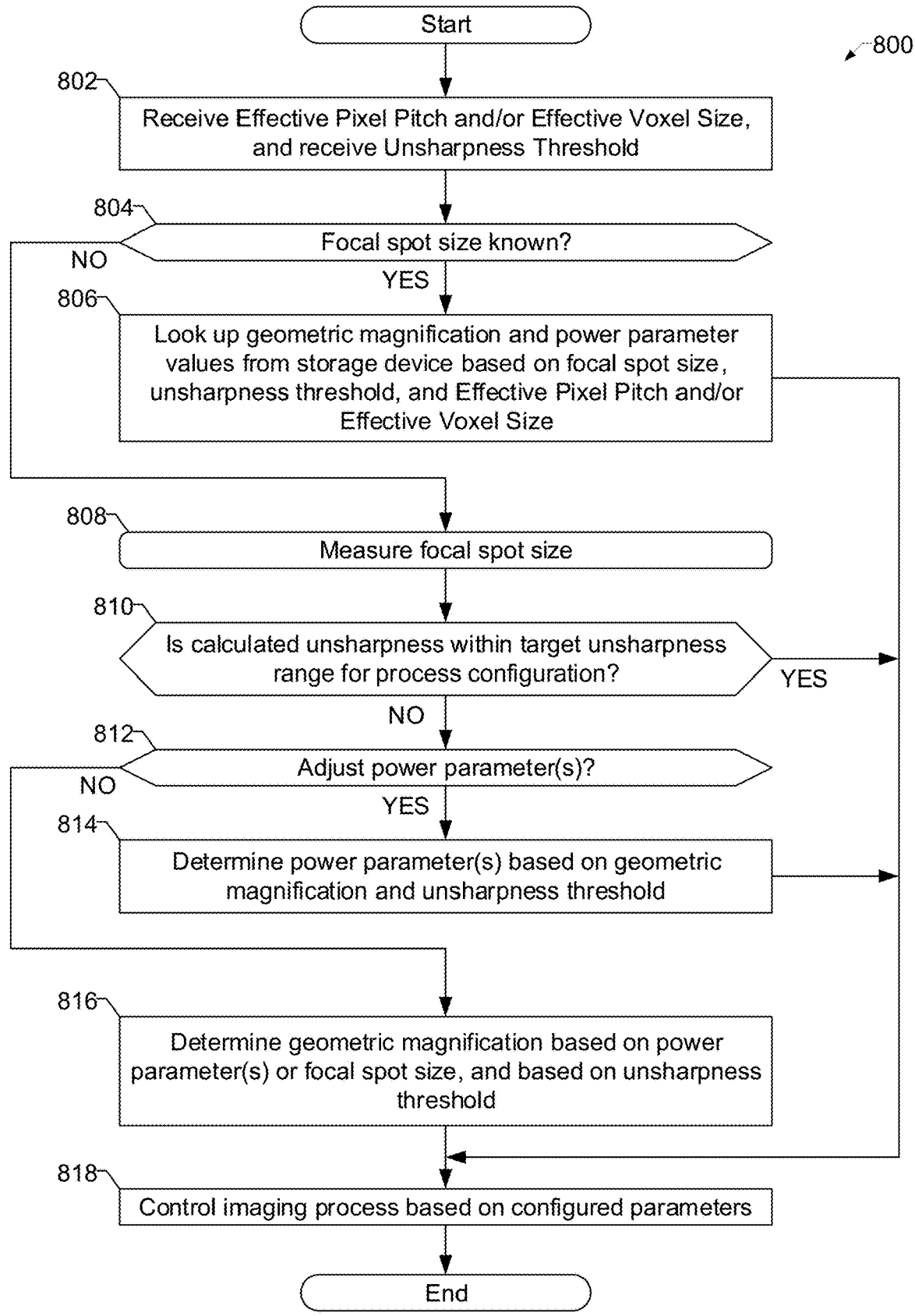
FIG. 8 is a flowchart representative of other example machine readable instructions which may be implemented by the example X-ray radiography system of FIGS. 1 and 2 to determine imaging parameters for a radiography process based on a specified pixel pitch and/or voxel size.

FIG. 8 is a flowchart representative of other example machine readable instructions 800 which may be implemented by the example X-ray radiography system 100 of FIGS. 1 and 2 to determine imaging parameters for a radiography process based on a specified effective pixel pitch and/or effective voxel size. The example instructions 800 may be stored on a storage device (e.g., the memory circuitry 212 of FIG. 2) and executed by processing circuitry (e.g., the processing circuitry 210 of FIG. 2). The instructions 800 may be performed, for example, in response to input of a voxel size input 410 and selection of the "Effective Pixel Pitch/Effective Voxel Size" button 420 via the interface 400.

At block 802, processing circuitry 210 receives (e.g., via the user interface 400 of FIG. 4) an effective pixel pitch and/or an effective voxel size, and receives an unsharpness threshold. In some examples, the unsharpness threshold may be calculated from the pixel pitch and/or the effective voxel size. The processing circuitry 210 may receive the pixel pitch and/or the effective voxel size, and the unsharpness threshold, via manual input and/or automatically from a remote computing system (e.g., the system 299 of FIG. 2).

At block 804, the processing circuitry 210 determines whether the focal spot size is known (e.g., previously measured or otherwise determined). For example, if the focal spot size was determined (e.g., measured) less than a threshold time prior to using a measured wattage, the processing circuitry 210 may look up the focal spot size in a reference table. If the focal spot size is known (block 804), at block 806 the processing circuitry 210 looks up geometric magnification and power parameter values from a storage device based on the focal spot size, unsharpness threshold, and pixel pitch and/or effective voxel size.

If the focal spot size is not known (block 804), at block 808 the processing circuitry 210 measures the focal spot size. Block 808 may be implemented by performing, for example, blocks 602-606 of FIG. 6.

At block 810, the processing circuitry 210 determines whether the calculated unsharpness is within a target unsharpness range for the process configuration. For example, an upper threshold of the target unsharpness range may be equivalent to, or based on, a pixel size or an effective pixel pitch, to cause the processing circuitry 210 to determine whether the unsharpness is less than the equivalent of one pixel. In other examples, the calculated unsharpness may be compared to a voxel size. However, any other desired threshold value may be used.

In some examples, the processing circuitry 210 may further determine in block 810 whether the calculated unsharpness is below an upper unsharpness threshold and/or above a lower unsharpness threshold. In some examples, the lower unsharpness threshold is determined as a threshold slightly (e.g., a predetermined amount or percentage of the threshold) below the upper unsharpness threshold, to thereby avoid an unnecessarily long process time to achieve effectively the same image quality.

If the calculated unsharpness is not within the target unsharpness range for the process configuration (block 810), at block 812 the processing circuitry 210 determines whether to adjust (e.g., correct) power parameter(s) (e.g., wattage, voltage, current). For example, the processing circuitry 210 may determine whether the geometric magnification is fixed and/or whether the operator has requested a recommendation for the power parameter(s). In some examples, the processing circuitry 210 determines whether to adjust (e.g., correct) the geometric magnification parameter instead of the power parameter(s). For example, the processing circuitry 210 may determine whether the power parameter(s) are fixed and/or whether the operator has requested a recommendation for the magnification.

If the power parameter(s) are to be adjusted (block 812), at block 814 the processing circuitry 210 determines one or more power parameters based on the geometric magnification and the unsharpness threshold. For example, the processing circuitry 210 may look up a wattage, a voltage, and/or a current in a reference table (e.g., the data 218 of FIG. 2) based on the geometric magnification and unsharpness threshold. In some examples, the determination may include interpolation between sets of data points in the table. The determination may further involve outputting an indication that the selected value(s) of the power parameter(s) result in the value of an unsharpness parameter satisfying the threshold unsharpness.

If the power parameter(s) are not to be corrected (block 812), at block 816 the processing circuitry 210 determines the geometric magnification based on one or more power parameters and the unsharpness threshold. For example, the processing circuitry 210 may look up a geometric magnification in a reference table (e.g., the data 218 of FIG. 2) based on the wattage, voltage, and/or current, and the unsharpness threshold. In some examples, the determination may include interpolation between sets of data points in the table. The determination may further involve outputting an indication that the selected value of the geometric magnification results in the value of an unsharpness parameter satisfying the threshold unsharpness.

After determining the geometric magnification correction (block 816), after determining the power parameter correction(s) (block 814), if none of the parameters are to be corrected (block 816), and/or after looking up the geometric magnification and power parameter values (block 806), at block 818 the processing circuitry 210 controls the imaging process based on the configured parameters. For example, the processing circuitry 210 controls the emitter 106 and detector 108 to generate one or more 2D and/or radiographs for 3D data (e.g., 3D CT scans, etc.) using the parameters recommended via block 806 or blocks 808-818 based on the measured focal spot size. The example instructions 800 then end.

In addition or as an alternative to automatically setting power parameter(s) and/or geometric magnification, the example X-ray radiography system 100 may guide an operator to select power parameter(s) and/or adjust geometric magnification by providing a calculated unsharpness and/or an indication of whether the unsharpness is within an acceptable range. The acceptable range may be determined, for example, based on a developed technique for the object 102. The acceptable range may have an upper unsharpness limit, a lower unsharpness limit, or both.

In an example of guiding an operator, the X-ray radiography system 100 may determine a focal spot size based on a reference image, in a similar or identical manner as described above. The X-ray radiography system 100 calculates the unsharpness value for a configured geometric magnification and for configured power parameter(s). The X-ray radiography system 100 may compare the calculated unsharpness value to the acceptable range, and output an indication of whether the power parameter value(s) and/or geometric magnification result in the value of the unsharpness parameter satisfying the acceptable unsharpness range. The indication may be output via the user interface 204, such as via a display, by displaying to the operator an icon or other text or graphic. The indication may inform the user of whether the calculated unsharpness is within the acceptable unsharpness range. If the calculated unsharpness is not within the acceptable range, the indication may further instruct the user on what parameter(s) and/or configuration(s) may be adjusted to adjust the unsharpness relative to the acceptable unsharpness range, and/or how to adjust the parameter(s) and/or configuration(s). For example, the user interface 204 may display only the result of the comparison of the calculated unsharpness value with the acceptable unsharpness range, or may further indicate that increasing the wattage will reduce an unsharpness that is higher than the acceptable range.

Figure 9:
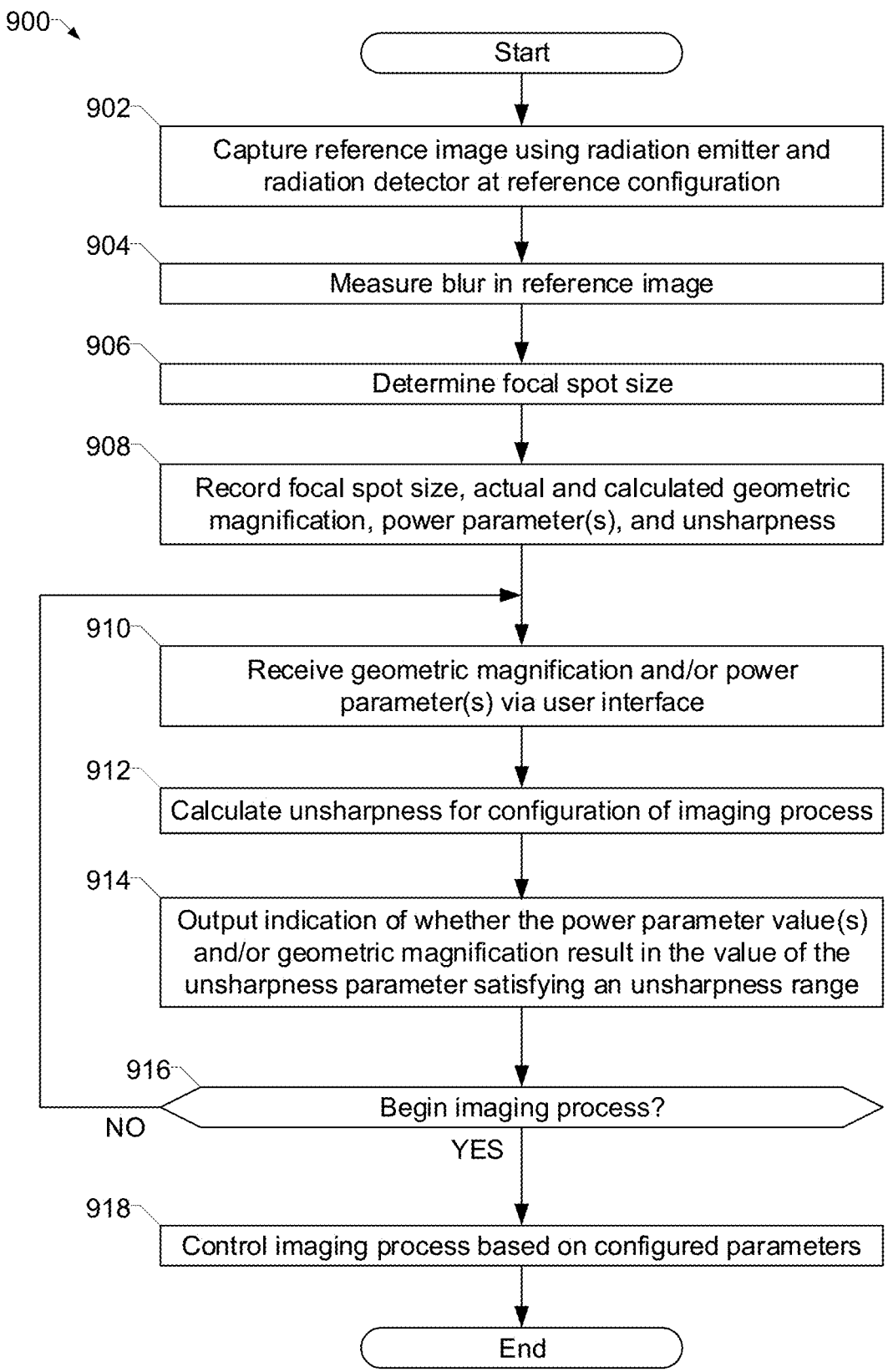
FIG. 9 is a flowchart representative of example machine readable instructions which may be implemented by the example X-ray radiography system of FIGS. 1 and 2 to provide guidance for imaging parameters for a radiography process based on a measured focal spot.

FIG. 9 is a flowchart representative of example machine readable instructions 900 which may be implemented by the example X-ray radiography system 100 of FIGS. 1 and 2 to provide guidance for imaging parameters for a radiography process based on a measured focal spot. The example instructions 900 may be stored on a storage device (e.g., the memory circuitry 212 of FIG. 2) and executed by processing circuitry (e.g., the processing circuitry 210 of FIG. 2).

At block 902, the X-ray detector 108 captures a reference image (e.g., the reference image 310 of FIG. 3A) at a reference configuration. For example, the reference configuration may involve a predetermined arrangement of the radiation emitter 106, a reference object 102 under inspection, and an X-ray detector 108. The predetermined arrangement may have been previously measured as a preferred arrangement to achieve an accurate measurement of blur and/or focal spot size.

At block 904, the processing circuitry 210 measures blur in the reference image 310. For example, the processing circuitry 210 may calculate an expected size 308 of the object in the reference image 310 and measure the actual size 312 of the object in the image. The processing circuitry 210 then determines the blur as half of the difference between the expected size 308 and actual size 312. The blur may be measured in multiple dimensions. At block 906, the processing circuitry 210 determines the focal spot size based on the measured blur.

At block 908, the processing circuitry 210 records the focal spot size, actual geometric magnification, calculated geometric magnification, emitter voltage, power parameter(s), and unsharpness (e.g., in a reference table). For example, in addition to recording the geometric magnification used to capture the reference image, the processing circuitry 210 may calculate and store a geometric magnification at which the determined focal spot size would obtain a predetermined unsharpness threshold. The recorded data may be used to update the reference table with current data.

Blocks 902-908 may be implemented in a similar or identical manner as blocks 602-608 of FIG. 6. In other examples, the processing circuitry 210 may use a different focal spot measurement position for the emitter 106, the detector 108, and/or the object positioner 110. During the focal spot measurement procedure, the processing circuitry 210 may store a geometric magnification value (e.g., entered by the operator, obtained from a stored technique, etc.) for subsequent use during the subsequent scan.

At block 910, the processing circuitry 210 receives a geometric magnification and/or power parameter(s) via the user interface 204. For example, the operator may input and modify a wattage and/or a configured geometric magnification. In some examples, the processing circuitry 210 may automatically calculate and/or store a current geometric magnification (e.g., prior to moving to a focal spot measurement position) based on the relative positions of the emitter 106, the X-ray detector 108, and the object positioner 110 and/or the rotatable fixture 112. The stored geometric magnification may correspond to the technique magnification, and the system 100 may be configured using the stored geometric magnification following the focal spot measurement(s).

At block 912, the processing circuitry 210 calculates the unsharpness for the configuration of an imaging process as input by the operator. For example, the processing circuitry 210 may determine the unsharpness at a same focal spot size for a same power parameter as during the focal spot measurement, using the same magnification or a different magnification, and/or may determine the unsharpness at a different focal spot size (e.g., based on a lookup table) for a same geometric magnification.

At block 914, the processing circuitry 210 outputs (e.g., via the user interface 204) an indication of whether the power parameter value(s) and/or the geometric magnification result in the value of the unsharpness parameter satisfying an unsharpness range. The indication may display to the operator whether the calculated unsharpness is within the unsharpness range and, if not within the range, instructions on how to change the parameter(s) and/or configuration to achieve an acceptable unsharpness. For example, the processing circuitry 210 may output instructions to increase or decrease the wattage and/or to increase or decrease the geometric magnification.

At block 916, the processing circuitry 210 determines whether to begin the imaging process. For example, the operator may command the X-ray radiography system 100 via the user interface 204 to begin a scan. If the imaging process is not started (block 916), control returns to block 910 to continue configuring the test and determining the unsharpness values.

When the imaging process is commanded to begin (block 916), at block 918 the processing circuitry 210 controls the imaging process based on the configured parameters. For example, the processing circuitry 210 controls the emitter 106 and detector 108 to generate one or more 2D and/or radiographs for 3D data (e.g., 3D CT scans, etc.) using the parameters set at block 910 by the operator. The example instructions 900 then end.

In some other examples, blocks 812-816 of FIG. 8 may be modified and/or replaced with outputting an indication of whether the selected power parameter(s) and/or geometric magnification result in an unsharpness value that is within an acceptable range (e.g., determined based on the effective pixel pitch and/or effective voxel size).

In yet other examples, the processing circuitry 210 may implement a loop in which the operator inputs the desired power parameters, focal spot size, and/or geometric magnification of the technique, the system 100 measures the actual focal spot size, and outputs an indication of whether the unsharpness is within an acceptable range. The operator may then adjust parameters and/or geometry, and re-measure the focal spot size, until the desired unsharpness range is reached. In some examples, the processing circuitry 210 may provide guidance to the operator for adjusting the parameters and/or geometry.

Figure 10:
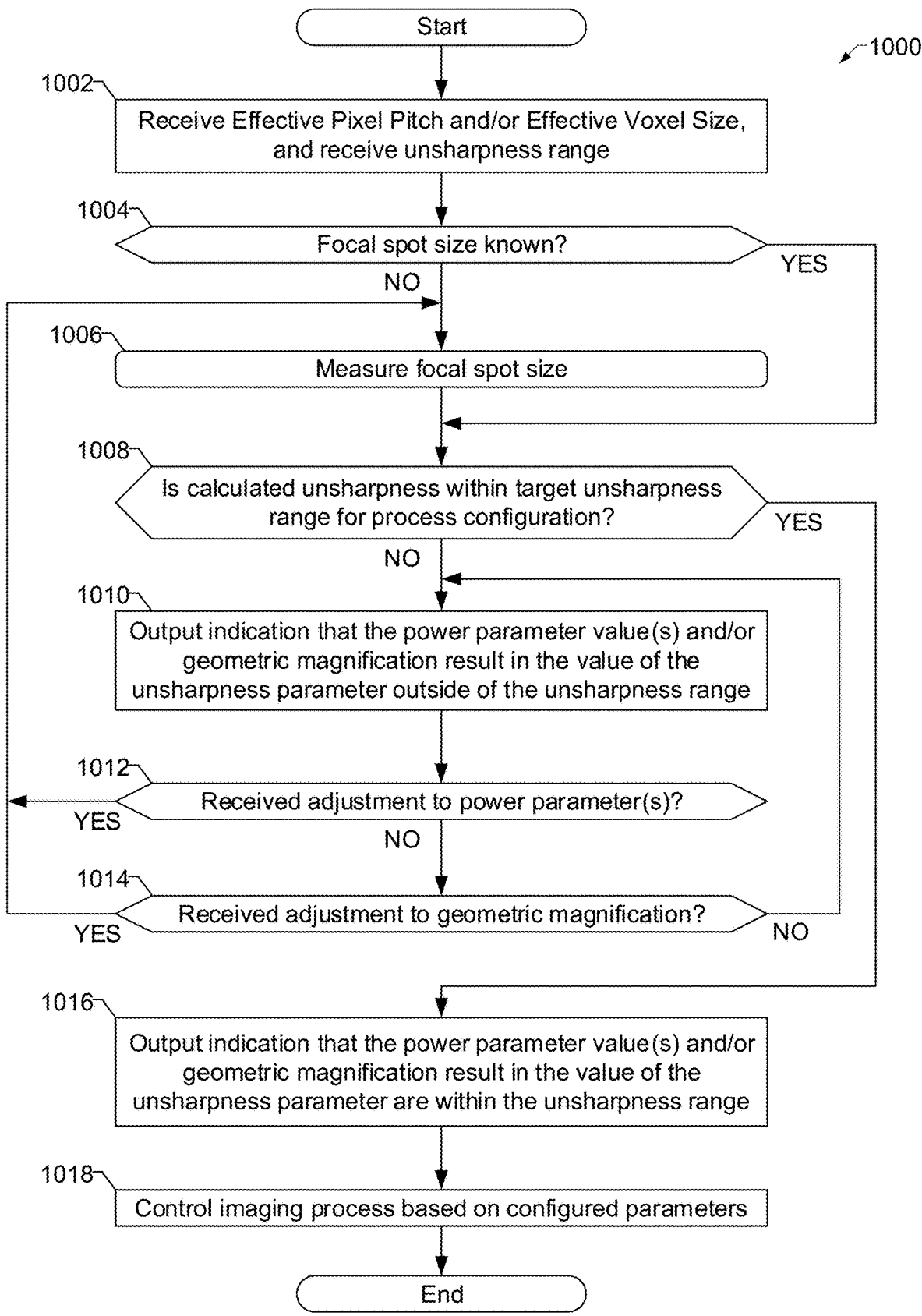
FIG. 10 is a flowchart representative of other example machine readable instructions which may be implemented by the example X-ray radiography system 100 of FIGS. 1 and 2 to provide guidance for imaging parameters for a radiography process based on a specified effective pixel pitch and/or effective voxel size.

FIG. 10 is a flowchart representative of other example machine readable instructions 1000 which may be implemented by the example X-ray radiography system 100 of FIGS. 1 and 2 to provide guidance for imaging parameters for a radiography process based on a specified effective pixel pitch and/or effective voxel size. The example instructions 1000 may be stored on a storage device (e.g., the memory circuitry 212 of FIG. 2) and executed by processing circuitry (e.g., the processing circuitry 210 of FIG. 2). The example instructions 1000 guide the selection of parameters and/or magnification by outputting an indication of whether a measured focal spot size and geometry result in a desired unsharpness (e.g., instead of automatic selection of parameters and/or magnification). The instructions 1000 may be performed, for example, in response to input of a voxel size input 410 and selection of the "Effective Pixel Pitch/Effective Voxel Size" button 420 via the interface 400.

At block 1002, processing circuitry 210 receives (e.g., via the user interface 400 of FIG. 4) an effective pixel pitch and/or an effective voxel size, and receives an unsharpness threshold. In some examples, the unsharpness threshold may be calculated from the pixel pitch and/or the effective voxel size. The processing circuitry 210 may receive the pixel pitch and/or the effective voxel size, and the unsharpness threshold, via manual input and/or automatically from a remote computing system (e.g., the system 299 of FIG. 2).

At block 1004, the processing circuitry 210 determines whether the focal spot size is known (e.g., previously measured or otherwise determined). For example, if the focal spot size was determined (e.g., measured) less than a threshold time prior to using a measured wattage, the processing circuitry 210 may look up the focal spot size in a reference table. If the focal spot size is known (block 1004), the processing circuitry 210 may look up geometric magnification and power parameter values from a storage device based on the focal spot size, unsharpness threshold, and pixel pitch and/or effective voxel size.

If the focal spot size is not known (block 1004), at block 1006 the processing circuitry 210 measures the focal spot size. Block 1006 may be implemented by performing, for example, blocks 602-606 of FIG. 6.

At block 1008, the processing circuitry 210 determines whether the calculated unsharpness is within a target unsharpness range for the process configuration. For example, an upper threshold of the target unsharpness range may be equivalent to, or based on, a pixel size or an effective pixel pitch, to cause the processing circuitry 210 to determine whether the unsharpness is less than the equivalent of one pixel. In other examples, the calculated unsharpness may be compared to a voxel size. However, any other desired threshold value may be used.

In some examples, the processing circuitry 210 may further determine in block 1008 whether the calculated unsharpness is below an upper unsharpness threshold and/or above a lower unsharpness threshold. In some examples, the lower unsharpness threshold is determined as a threshold slightly (e.g., a predetermined amount or percentage of the threshold) below the upper unsharpness threshold, to thereby avoid an unnecessarily long process time to achieve effectively the same image quality.

If the calculated unsharpness is not within the target unsharpness range for the process configuration (block 1008), at block 1010 the processing circuitry 210 outputs (e.g., via the user interface 204) an indication that the power parameter value(s) and/or the geometric magnification result in the value of the unsharpness parameter that is outside of the unsharpness range.

At block 1012, the processing circuitry 210 determines whether adjustment(s) to the power parameter(s) have been received (e.g., via the user interface 204). For example, the operator may select different values of the wattage or other power parameters to change the focal spot and the unsharpness. Alternatively, the processing circuitry 210 may make a correction to the power parameter(s) based on stored relationships between the power parameter(s) and the unsharpness (or focal spot).

If an adjustment to the power parameter(s) has not been received or determined (block 1012), at block 1014 the processing circuitry 210 determines whether adjustment(s) to the geometric magnification have been received (e.g., via the user interface 204). For example, the operator may select different values of the geometric magnification via the user interface 204 and/or adjust the geometry of the emitter 106, the detector 108, and/or the object positioner 210, from which the processing circuitry 210 may calculate the geometric magnification. Alternatively, the processing circuitry 210 may make a correction to the geometric magnification (and/or configured geometry of the system 100) based on stored relationships between the magnification and the unsharpness (or focal spot).

If an adjustment to the geometric magnification has not been received or determined (block 1014), control returns to block 1010 to continue outputting the indication that the unsharpness is outside of the range. On the other hand, when an adjustment to the power parameter(s) has been received or determined (block 1012), or an adjustment to the geometric magnification has been received or determined (block 1014), control returns to block 1006 to re-measure the focal spot size.

When the calculated unsharpness is within the target unsharpness range (block 1008), at block 1016 the processing circuitry 210 outputs (e.g., via the user interface 204) an indication that the power parameter value(s) and/or the geometric magnification result in the value of the unsharpness parameter that is within the unsharpness range.

At block 1018 the processing circuitry 210 controls the imaging process based on the configured parameters. For example, the processing circuitry 210 controls the emitter 106 and detector 108 to generate one or more 2D and/or radiographs for 3D data (e.g., 3D CT scans, etc.). The example instructions 1000 then end.

The present methods and/or systems may be realized in hardware, software, or a combination of hardware and software. The present methods and/or systems may be realized in a centralized fashion in at least one computing system, or in a distributed fashion where different elements are spread across several interconnected computing and/or remote computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more instructions (e.g., lines of code) executable by a machine, thereby causing the machine to perform processes as described herein.

As utilized herein, the terms "e.g.," and "for example" set off lists of one or more non-limiting examples, instances, or illustrations.

As used herein, the terms "coupled," "coupled to," and "coupled with," each mean a structural and/or electrical connection, whether attached, affixed, connected, joined, fastened, linked, and/or otherwise secured. As used herein, the term "attach" means to affix, couple, connect, join, fasten, link, and/or otherwise secure. As used herein, the term "connect" means to attach, affix, couple, join, fasten, link, and/or otherwise secure.

As used herein the terms "circuits" and "circuitry" refer to physical electronic components (i.e., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" and/or "configured" to perform a function whenever the circuitry comprises the necessary hardware and/or code (if any is necessary) to perform the function, regardless of whether performance of the function is disabled or enabled (e.g., by a user-configurable setting, factory trim, etc.).

As used herein, a control circuit may include digital and/or analog circuitry, discrete and/or integrated circuitry, microprocessors, DSPs, etc., software, hardware and/or firmware, located on one or more boards, that form part or all of a controller, and/or are used to control a radiography system to perform a radiography process.

As used herein, the term "processor" means processing devices, apparatus, programs, circuits, components, systems, and subsystems, whether implemented in hardware, tangibly embodied software, or both, and whether or not it is programmable. The term "processor" as used herein includes, but is not limited to, one or more computing devices, hardwired circuits, signal-modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing. The processor may be, for example, any type of general purpose microprocessor or microcontroller, a digital signal processing (DSP) processor, an application-specific integrated circuit (ASIC), a graphic processing unit (GPU), a reduced instruction set computer (RISC) processor with an advanced RISC machine (ARM) core, etc. The processor may be coupled to, and/or integrated with a memory device.

As used, herein, the term "memory," "memory circuitry," and/or "memory device" means computer hardware or circuitry to store information for use by a processor and/or other digital device. The memory, memory circuitry, and/or memory device can be any suitable type of computer memory or any other type of electronic storage medium, such as, for example, read-only memory (ROM), random access memory (RAM), cache memory, compact disc read-only memory (CDROM), electro-optical memory, magneto-optical memory, programmable read-only memory (PROM), erasable programmable read-only memory (EPROM), electrically-erasable programmable read-only memory (EEPROM), a computer-readable medium, or the like. Memory can include, for example, a non-transitory memory, a non-transitory processor readable medium, a non-transitory computer readable medium, non-volatile memory, dynamic RAM (DRAM), volatile memory, ferroelectric RAM (FRAM), first-in-first-out (FIFO) memory, last-in-first-out (LIFO) memory, stack memory, non-volatile RAM (NVRAM), static RAM (SRAM), a cache, a buffer, a semiconductor memory, a magnetic memory, an optical memory, a flash memory, a flash card, a compact flash card, memory cards, secure digital memory cards, a microcard, a minicard, an expansion card, a smart card, a memory stick, a multimedia card, a picture card, flash storage, a subscriber identity module (SIM) card, a hard drive (HDD), a solid state drive (SSD), etc. The memory can be configured to store code, instructions, applications, software, firmware and/or data, and may be external, internal, or both with respect to the processor.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations.

While the present methods and/or systems have been described with reference to certain implementations, it will be understood by those skilled in the art that various changes may be made, and equivalents may be substituted without departing from the scope of the present method and/or system. For example, blocks and/or components of disclosed examples may be combined, divided, re-arranged, and/or otherwise modified. In addition, many modifications may be made to adapt a particular situation or material to the teachings of the present disclosure without departing from its scope. Therefore, the present methods and/or systems are not limited to the particular implementations disclosed. Instead, the present methods and/or systems will include all implementations falling within the scope of the appended claims, both literally and under the doctrine of equivalents.

What is claimed is:

1. A method to configure a radiography system having a radiation emitter and a radiation detector, the method comprising:

analyzing, using processing circuitry, a reference image captured using a first value of a first power parameter for the radiation emitter to determine a value of a focal spot size for the radiation emitter;

based on a determined relationship between the first value of the first power parameter and the value of the focal spot size, output an indication of whether a selected value of the first power parameter results in a value of an unsharpness parameter satisfying a threshold unsharpness value; and control the radiography system using the selected power parameter to perform a radiography process to obtain one or more radiographic images that satisfy the threshold unsharpness value.

2. The method as defined in claim 1, further comprising receiving an updated value of the first power parameter, and outputting an indication of whether the updated value of the first power parameter results in the value of the unsharpness parameter satisfying the threshold unsharpness value.

3. The method as defined in claim 1, further comprising outputting a recommended change to the value of the first power parameter to cause the value of the first power parameter to result in the value of the unsharpness parameter satisfying the threshold unsharpness value.

4. The method as defined in claim 1, further comprising outputting an indication of whether a detected magnification value results in the value of the unsharpness parameter satisfying a threshold unsharpness value.

5. The method as defined in claim 4, further comprising outputting a recommended change to the magnification value to cause the value of the first power parameter to result in the value of the unsharpness parameter satisfying the threshold unsharpness value.

6. The method as defined in claim 1, wherein the threshold unsharpness value is based on at least one of a pixel size of the radiation detector or a pixel pitch of the radiation detector.

7. The method as defined in claim 1, wherein the threshold unsharpness value is set to one of a dimension of a pixel of the radiation detector or a pixel pitch of the radiation detector.

8. The method as defined in claim 1, wherein the analyzing of the reference image comprises analyzing the reference image to determine one or more dimensions of a reference feature based on a predetermined gauge device.

9. The method as defined in claim 8, further comprising:
measuring one or more dimensions of blur in the reference image; and
storing the one or more dimensions in a storage device in association with at least one of the first power parameter, a location of the measurement on the reference image, the current focal spot size, a voxel size, an effective pixel pitch, or a magnification parameter.

10. The method as defined in claim 1, wherein the radiation emitter comprises an X-ray tube and the radiation detector comprises a digital X-ray detector.

11. The method as defined in claim 1, further comprising:
determining the value of the unsharpness parameter based on the measured focal spot size and a magnification parameter.

12. A radiography system, comprising:
a user interface;
a radiation detector;
a radiation emitter configured to emit radiation toward the radiation detector;
an object positioner configured to position an object-under-inspection between the radiation detector and the radiation emitter; and
a computing device comprising processing circuitry configured to:
analyze a reference image captured using a first value of a first power parameter for the radiation emitter to determine a value of a focal spot size for the radiation emitter;
based on a determined relationship between the first value of the first power parameter and the value of the focal spot size, output, via the user interface, an indication of whether a selected value of the first power parameter results in a value of an unsharpness parameter satisfying a threshold unsharpness value; and
control the radiation emitter using the selected power parameter to perform a radiography process to obtain one or more radiographic images that satisfy the threshold unsharpness value.

13. The radiography system as defined in claim 12, wherein the user interface is configured to receiving an updated value of the first power parameter, and the processing circuitry is configured to output an indication of whether the updated value of the first power parameter results in the value of the unsharpness parameter satisfying the threshold unsharpness value.

14. The radiography system as defined in claim 12, wherein the processing circuitry is configured to output a recommended change to the value of the first power parameter to cause the value of the first power parameter to result in the value of the unsharpness parameter satisfying the threshold unsharpness value.

15. The radiography system as defined in claim 12, wherein the processing circuitry is configured to output an indication of whether a detected magnification value results in the value of the unsharpness parameter satisfying a threshold unsharpness value.

16. The radiography system as defined in claim 15, wherein the processing circuitry is configured to output a recommended change to the magnification value to cause the value of the first power parameter to result in the value of the unsharpness parameter satisfying the threshold unsharpness value.

17. The radiography system as defined in claim 12, wherein the threshold unsharpness value is based on at least one of a pixel size of the radiation detector or a pixel pitch of the radiation detector.

18. The radiography system as defined in claim 12, wherein the threshold unsharpness value is set to one of a dimension of a pixel of the radiation detector or a pixel pitch of the radiation detector.

19. The radiography system as defined in claim 12, wherein the processing circuitry is configured to analyze the reference image by analyzing the reference image to determine one or more dimensions of a reference feature based on a predetermined gauge device.

20. The radiography system as defined in claim 19, wherein the processing circuitry is configured to:
measure one or more dimensions of blur in the reference image; and
store the one or more dimensions in a storage device in association with at least one of the first power parameter, a location of the measurement on the reference image, the current focal spot size, a voxel size, an effective pixel pitch, or a magnification parameter.

* * * * *